US012778565B2

(12) United States Patent
Rolando et al.

(10) Patent No.: US 12,778,565 B2
(45) Date of Patent: Nov. 3, 2026

(54) CROSSABLE INTERSEPTAL OCCLUDER DEVICE

(71) Applicant: RECROSS CARDIO INC., Dover, DE (US)

(72) Inventors: Giovanni Rolando, Milan (IT); Marta Antonucci, Milan (IT); Simona Roggero, Milan (IT)

(73) Assignee: RECROSS CARDIO INC., Dover, DE (US)

( * ) Notice: Subject to any disclaimer, the term of this patent is extended or adjusted under 35 U.S.C. 154(b) by 575 days.

(21) Appl. No.: 17/608,466

(22) PCT Filed: May 4, 2020

(86) PCT No.: PCT/IB2020/054195
§ 371 (c)(1),
(2) Date: Nov. 2, 2021

(87) PCT Pub. No.: WO2020/225698
PCT Pub. Date: Nov. 12, 2020

(65) Prior Publication Data

US 2022/0211361 A1 Jul. 7, 2022

(30) Foreign Application Priority Data

May 3, 2019 (IT) ........................ 102019000006534

(51) Int. Cl.
*A61B 17/00* (2006.01)

(52) U.S. Cl.
CPC *A61B 17/0057* (2013.01); *A61B 2017/00526* (2013.01); *A61B 2017/00592* (2013.01);
(Continued)

(58) Field of Classification Search
CPC A61B 2017/00592; A61B 2017/00597; A61B 2017/00606
See application file for complete search history.

(56) References Cited

U.S. PATENT DOCUMENTS 4,007,743 A 2/1977 Blake
4,964,850 A * 10/1990 Bouton ............... A61M 27/002 604/106

(Continued)

FOREIGN PATENT DOCUMENTS

AU 4352497 4/1998
CN 1736346 2/2006

(Continued)

OTHER PUBLICATIONS

International Search Report, issued in PCT/IB2020/054195, mailed Aug. 25, 2020, Rijswijk, Netherlands.

(Continued)

*Primary Examiner* — Alexander J Orkin
(74) *Attorney, Agent, or Firm* — Knobbe, Martens, Olson & Bear, LLP

(57) ABSTRACT

A crossable interseptal occluder device has a support structure having a central support structure portion delimiting a lumen, anchoring portions, and is configured to contract and expand between a compressed configuration and an expanded configuration in which the anchoring portions extend radially outwards from the central support structure portion to compress a partition by arranging the support structure astride the partition through a defect or hole. A diaphragm configured to close the majority of the lumen when the diaphragm is in a relaxed configuration, allows a medical device inserted into a first compartment delimited by the partition to pass through the diaphragm and the lumen entering a second compartment. The diaphragm has a plurality of occluding bridges, each having an elongated body with body ends and longitudinal edges. In the relaxed configuration of the diaphragm, each occluding bridge is arranged close to a further occluding bridge. A portion of the
(Continued)

longitudinal edges of each occluding bridge and of the further occluding bridge delimit a slit or cut.

19 Claims, 16 Drawing Sheets

(52) U.S. Cl.
CPC ............... *A61B 2017/00597* (2013.01); *A61B 2017/00606* (2013.01)

(56) References Cited

U.S. PATENT DOCUMENTS 5,108,420 A 4/1992 Marks
5,425,744 A 6/1995 Fagan et al.
6,171,329 B1 1/2001 Shaw
6,206,907 B1 3/2001 Marino et al.
6,379,368 B1 4/2002 Corcoran et al.
6,712,836 B1 3/2004 Berg
7,665,466 B2 2/2010 Figulla et al.
7,842,069 B2 11/2010 Widomski et al.
8,277,482 B2 10/2012 Hruska et al.
8,323,312 B2 12/2012 Clark
8,752,258 B2 6/2014 Finch et al.
8,870,913 B2 10/2014 Opolski et al.
9,179,899 B2 11/2015 Freudenthal
9,332,976 B2 5/2016 Yribarren
9,414,823 B2 8/2016 Ben Hamou et al.
9,445,797 B2 9/2016 Rothstein et al.
9,456,812 B2 10/2016 Finch et al.
9,532,772 B2 1/2017 Moszner et al.
9,554,783 B2 1/2017 Pavcnik et al.
9,668,742 B2 6/2017 Blum et al.
9,840,577 B2 12/2017 Singhal et al.
9,877,710 B2 1/2018 Amplatz et al.
9,937,036 B2 4/2018 Sugimoto et al.
10,265,059 B2 4/2019 Rowe et al.
10,893,854 B2 1/2021 Joyeux
11,006,938 B2 5/2021 Coyle et al.
11,045,178 B2 6/2021 Onushko et al.
11,071,533 B2 7/2021 Rothstein et al.
11,259,789 B2 3/2022 Rowe et al.
11,337,684 B2 5/2022 Zhang et al.
11,439,396 B2 9/2022 Johnson et al.
11,712,230 B2 8/2023 Johnson et al.
11,832,805 B2 12/2023 Eidenschink et al.
11,839,381 B2 12/2023 Persyzk et al.
11,911,272 B2 2/2024 Chan et al.
11,998,183 B2 6/2024 Eidenschink et al.
12,059,142 B2 8/2024 Eidenschink et al.
12,102,310 B2 10/2024 Rowe et al.
12,127,739 B2 10/2024 Rothstein et al.
12,171,418 B2 12/2024 Dudzinski et al.
12,178,419 B2 12/2024 Coyle et al.
12,232,738 B2 2/2025 Persyzk et al.
12,303,132 B2 5/2025 Johnson et al.
12,349,884 B2 7/2025 Eidenschink et al.
12,364,468 B2 7/2025 Eidenschink et al.
12,433,599 B2 10/2025 Persyzk et al.
12,478,362 B2 11/2025 Johnson et al.
12,514,707 B2 1/2026 Cole et al.
2001/0039450 A1 11/2001 Pavcnik et al.
2002/0042565 A1* 4/2002 Cooper ..................... A61F 2/92 600/407
2003/0070682 A1* 4/2003 Wilson .................. A61F 2/2412 128/207.16
2004/0143291 A1 7/2004 Corcoran
2004/0143292 A1 7/2004 Marino
2004/0143294 A1 7/2004 Corcoran
2005/0027261 A1* 2/2005 Weaver ................. A61M 39/24 604/246
2005/0113868 A1 5/2005 Devellian et al.
2005/0171489 A1* 8/2005 Weaver ................. A61M 39/24 604/247
2005/0267524 A1 12/2005 Chanduszko
2005/0288706 A1 12/2005 Widomski
2007/0043391 A1 2/2007 Moszner et al.
2007/0073337 A1 3/2007 Abbott et al.
2008/0033478 A1 2/2008 Meng
2008/0051830 A1* 2/2008 Eidenschink .... A61B 17/12122 606/213
2008/0077180 A1 3/2008 Kladakis et al.
2008/0147111 A1 6/2008 Johnson
2008/0195123 A1 8/2008 Gainor et al.
2009/0177187 A1* 7/2009 Weaver Quigley ... F16K 15/147 137/845
2010/0057192 A1* 3/2010 Celermajer ............ A61B 17/11 623/1.26
2010/0222810 A1 9/2010 Debeer et al.
2011/0082495 A1* 4/2011 Ruiz .................. A61B 17/0057 606/213
2011/0184439 A1 7/2011 Anderson et al.
2011/0224720 A1 9/2011 Kassab et al.
2011/0257723 A1 10/2011 McNamara
2011/0306916 A1* 12/2011 Nitzan .................. A61F 2/2412 604/9
2012/0053686 A1* 3/2012 McNamara ........ A61B 17/0057 623/2.36
2012/0150218 A1 6/2012 Sandgren et al.
2012/0253386 A1* 10/2012 Rowe ..................... A61B 17/02 606/213
2012/0265296 A1 10/2012 McNamara et al.
2013/0073029 A1 3/2013 Shaw
2013/0190861 A1 7/2013 Chau et al.
2014/0012368 A1 1/2014 Sugimoto et al.
2014/0074155 A1 3/2014 Rothstein et al.
2014/0107618 A1* 4/2014 Hamboly .............. A61M 39/24 604/513
2014/0163449 A1 6/2014 Rottenberg et al.
2014/0194971 A1 7/2014 McNamara
2014/0296908 A1 10/2014 Ottma et al.
2014/0309684 A1 10/2014 Al-Qbandi et al.
2015/0112383 A1 4/2015 Sherman et al.
2015/0142049 A1* 5/2015 Delgado ............ A61B 17/3468 606/216
2015/0148731 A1 5/2015 McNamara
2015/0201945 A1 7/2015 Wojay
2015/0216653 A1* 8/2015 Freudenthal .......... A61F 2/2409 623/2.17
2015/0313599 A1* 11/2015 Johnson ............. A61B 17/0057 606/191
2015/0315399 A1 11/2015 Bredt et al.
2016/0022423 A1 1/2016 McNamara et al.
2016/0220357 A1* 8/2016 Anand ............... A61B 17/0057
2016/0262768 A1 9/2016 Haverkost
2016/0296684 A1 10/2016 Tamburino
2017/0014115 A1 1/2017 Rafiee et al.
2017/0079630 A1 3/2017 Xie et al.
2017/0224323 A1 8/2017 Rowe et al.
2017/0231766 A1 8/2017 Hariton et al.
2018/0333150 A1 11/2018 Bak-Boychuk et al.
2018/0339141 A1 11/2018 Scheule
2019/0099589 A1* 4/2019 Walsh ................. A61M 27/002
2019/0328374 A1 10/2019 Hendsbee
2020/0179663 A1 6/2020 McDaniel
2020/0197178 A1 6/2020 Vecchio
2020/0368505 A1 11/2020 Nae et al.
2021/0059684 A1 3/2021 Meyer et al.
2022/0175364 A1 6/2022 Rowe et al.
2022/0183694 A1 6/2022 Pan et al.

FOREIGN PATENT DOCUMENTS

CN 104042257 9/2014
CN 104224246 12/2014
CN 104414692 3/2015
CN 105054980 11/2015
CN 107397561 11/2017
CN 108451570 8/2018
CN 108714038 10/2018
DE 4222291 1/1994
DE 102005053958 5/2007

(56) References Cited

FOREIGN PATENT DOCUMENTS

| | | |
|---|---|---|
| DE | 102010019365 | 6/2011 |
| DE | 102014006984 | 11/2015 |
| EP | 0 653 921 | 5/1995 |
| EP | 0 655 222 | 6/1998 |
| EP | 0 541 063 | 9/1998 |
| EP | 0 545 091 | 7/1999 |
| EP | 0 861 049 | 4/2001 |
| EP | 1 149 561 | 10/2001 |
| EP | 1 210 014 | 6/2002 |
| EP | 1 474 043 | 11/2004 |
| EP | 1 509 144 | 3/2005 |
| EP | 0 888 083 | 6/2005 |
| EP | 1 538 994 | 6/2005 |
| EP | 1 595 504 | 11/2005 |
| EP | 1 641 400 | 4/2006 |
| EP | 1 670 345 | 6/2006 |
| EP | 1 673 132 | 6/2006 |
| EP | 1 018 943 | 10/2006 |
| EP | 1 737 349 | 1/2007 |
| EP | 0 947 165 | 7/2007 |
| EP | 1 718 213 | 7/2007 |
| EP | 0 876 793 | 12/2007 |
| EP | 1 928 327 | 6/2008 |
| EP | 1 948 037 | 7/2008 |
| EP | 1 965 706 | 9/2008 |
| EP | 1 605 865 | 12/2008 |
| EP | 1 836 969 | 6/2009 |
| EP | 1 765 180 | 11/2009 |
| EP | 2 140 815 | 1/2010 |
| EP | 2 066 241 | 6/2010 |
| EP | 2 056 723 | 7/2010 |
| EP | 1 955 661 | 3/2011 |
| EP | 1 842 490 | 9/2011 |
| EP | 2 427 123 | 3/2012 |
| EP | 2 528 646 | 12/2012 |
| EP | 2 029 029 | 3/2013 |
| EP | 2 062 540 | 4/2013 |
| EP | 2 481 356 | 9/2013 |
| EP | 2 642 954 | 10/2013 |
| EP | 2 451 361 | 11/2013 |
| EP | 2 688 630 | 1/2014 |
| EP | 2 311 380 | 4/2014 |
| EP | 2 744 423 | 6/2014 |
| EP | 2 531 113 | 12/2014 |
| EP | 2 116 190 | 9/2015 |
| EP | 2 043 527 | 10/2015 |
| EP | 2 967 867 | 1/2016 |
| EP | 2 623 039 | 7/2016 |
| EP | 3 069 661 | 9/2016 |
| EP | 1 469 790 | 10/2016 |
| EP | 2 398 395 | 5/2017 |
| EP | 2 757 962 | 6/2017 |
| EP | 2 108 315 | 9/2017 |
| EP | 2 819 585 | 11/2017 |
| EP | 3 054 855 | 11/2017 |
| EP | 3 253 297 | 12/2017 |
| EP | 3 297 541 | 3/2018 |
| EP | 2 688 486 | 5/2018 |
| EP | 3 329 860 | 6/2018 |
| EP | 2 004 068 | 8/2018 |
| EP | 3 367 917 | 9/2018 |
| EP | 2 753 246 | 11/2018 |
| EP | 3 398 533 | 11/2018 |
| EP | 3 398 537 | 11/2018 |
| EP | 2 259 728 | 3/2019 |
| EP | 3 071 118 | 8/2019 |
| EP | 3 151 753 | 9/2019 |
| EP | 2 207 500 | 10/2019 |
| EP | 2 744 412 | 10/2019 |
| EP | 3 146 937 | 10/2019 |
| EP | 2 952 157 | 1/2020 |
| EP | 1 827 247 | 4/2020 |
| EP | 2 999 412 | 5/2020 |
| EP | 2 422 709 | 6/2020 |
| EP | 2 757 957 | 11/2020 |
| EP | 2 416 736 | 12/2020 |
| EP | 3 122 284 | 1/2021 |
| EP | 2 731 510 | 4/2021 |
| EP | 2 741 679 | 10/2021 |
| FR | 2 305 165 | 10/1976 |
| FR | 2 714 284 | 3/1996 |
| FR | 2 827 153 | 1/2003 |
| GB | 2 407 985 | 5/2005 |
| WO | WO 1998/008462 | 3/1998 |
| WO | WO 2001/010306 | 2/2001 |
| WO | WO 2002/096295 | 12/2002 |
| WO | WO 2004/066811 | 8/2004 |
| WO | WO 2004/067092 | 8/2004 |
| WO | WO 2005/027752 | 3/2005 |
| WO | WO 2005/055834 | 6/2005 |
| WO | WO 2007/035726 | 3/2007 |
| WO | WO 2007/083288 | 7/2007 |
| WO | WO 2007/092274 | 8/2007 |
| WO | WO 2008/010738 | 1/2008 |
| WO | WO 2008/019590 | 2/2008 |
| WO | WO 2008/042229 | 4/2008 |
| WO | WO 2008/085235 | 7/2008 |
| WO | WO 2008/124603 | 10/2008 |
| WO | WO 2009/035610 | 3/2009 |
| WO | WO 2009/042866 | 4/2009 |
| WO | WO 2009/091425 | 7/2009 |
| WO | WO 2009/137755 | 11/2009 |
| WO | WO 2010/006061 | 1/2010 |
| WO | WO 2010/139771 | 12/2010 |
| WO | WO 2011/109792 | 9/2011 |
| WO | WO 2013/037005 | 3/2013 |
| WO | WO 2013/175468 | 11/2013 |
| WO | WO 2015/059567 | 4/2015 |
| WO | WO 2016/087061 | 6/2016 |
| WO | WO 2016/192781 | 12/2016 |
| WO | 2017136287 A1 | 8/2017 |
| WO | WO 2018/085545 | 5/2018 |
| WO | WO 2018/166377 | 9/2018 |
| WO | WO 2018/213230 | 11/2018 |
| WO | WO 2020/225698 | 11/2020 |
| WO | WO 2020/247907 | 12/2020 |
| WO | WO 2021/050589 | 3/2021 |
| WO | WO 2021/146342 | 7/2021 |
| WO | WO 2022/091018 | 5/2022 |
| WO | WO 2022/091019 | 5/2022 |

OTHER PUBLICATIONS

International Written Opinion, issued in PCT/IB2020/054195, mailed Aug. 25, 2020, Rijswijk, Netherlands.

International Preliminary Report on Patentability, issued in PCT/IB2020/054195.

* cited by examiner

CROSSABLE INTERSEPTAL OCCLUDER DEVICE

CROSS-REFERENCE TO RELATED APPLICATIONS

This application is a National Phase Application of PCT International Application No. PCT/IB2020/054195, having an International Filing Date of May 4, 2020 which claims the benefit of priority to Italian Patent Application No. 102019000006534, filed May 3, 2019, each of which is hereby incorporated by reference in its entirety.

FIELD OF THE INVENTION

In the most general aspect thereof, the present invention is directed to an occluder device. In particular, the present invention relates to an interseptal occluder device. Even more particularly, the present invention relates to an interseptal occluder device of the crossable type, or crossable interseptal occluder device.

In particular, the present invention is directed to a device for closing a defect of a partition or an opening obtained in a partition, not necessarily of the heart.

Even more particularly, the present invention is directed to a device for closing a defect present in a partition, for example a defect in an atrial partition, so that the defect, even if occluded, may be used for a medical device to pass through said defect.

Moreover, the device of the present invention is intended to occlude defects (typically congenital defects, but not only) or interatrial partition holes/openings created following percutaneous interventions with trans-septal puncture techniques (for example for the mitral valve repair or the occlusion of the Left Atrial Appendage).

BACKGROUND OF THE INVENTION

A partition is for example a thin wall dividing a cavity into two smaller cavities or chambers or compartments. The term “partition” is intended to define both a heart wall which divides two atria, as well as a wall which divides the right or left atrium and ventricle.

With reference to FIG. 1, an atrial partition 100 is a tissue wall which separates the right atrium 101 from the left atrium 102 of the heart 103.

A ventricular partition 104 is a tissue wall which separates the right 105 and left 106 ventricles of the heart 103.

A defect 107 of the partition 100, 104 may include a perforation or a hole in the partition. A defect 107 of the partition 100, 104 can occur congenitally or by piercing the partition with a medical device to access a position within the heart.

The femoral vein is an access point for many laboratory catheterization procedures, with a smaller percentage of procedures using the access to arteries.

The atrial partition 100 is a percutaneous access point, for example for atrial fibrillation therapy, closure of the left atrial appendage, percutaneous repair of the mitral valve, and percutaneous replacement of the mitral valve. In these and other procedures, the devices need to cross the atrial partition 100 and, in doing so, can leave an orifice in the atrial partition which cannot close or heal on its own.

Therefore, these defects are often closed using devices, such as clips or occluders. However, these devices do not allow re-crossing through the partition.

Therefore, there is a need for improved occlusion devices for closing a defect or an opening of the partition, and for re-crossing it in (possible) subsequent procedures.

Crossable occluding devices are known from the prior art. These have an anchoring structure and a diaphragm or valve connected thereto.

For example, documents WO2017136287A1, US2014074155 show crossable occluder solutions.

Document US20070073337 shows devices and methods for occluding the defects of internal tissues, such as the defects of the partition, with clip-based devices. A device having a clip structure is shown, which includes a tubular body having at least a first and a second deflectable element coupled thereto. The first and second elements are coupled at the opposite ends of the tubular body and configured to switch from a non-deployed configuration to a deployed configuration. In the deployed configuration, each element extends outwardly away from the tubular body in a position configured to rest on a tissue surface. The first and second elements of the clip are preferably configured to support a tissue wall therebetween and close any opening in the tissue wall. This solution does not allow to re-cross the device once implanted.

Document US20140012368 shows devices and methods for improving the implantation, retractability, or repositioning of a device for positioning a valve in a partition. The embodiments of the devices include pivotable sections which provide the ability to maintain the engagement of the device with a release system during implantation, in which the release system approaches an opening of the partition. The embodiments of the devices include configurations which allow for better recovery in a delivery system if a malfunction or problem with the patient’s physiology is detected. This device is used to implant a flow control valve. These solutions are devices for treating heart failure. In particular, it is intended to create interatrial pressure outlets, shunts, and the like, which reduce the high pressure on one side of the heart, thus mitigating the resulting symptoms. Therefore, this solution aims to create an opening in the partition. This flow control element is a tissue valve such as a tricuspid valve, a bicuspid valve or a single-leaflet valve made of pericardial tissue from cattle, pigs, sheep or other animals, and therefore it has cusp-like foils made of preferably natural tissue and cusp-shaped.

Document US20160296684 shows endoluminal devices for the treatment of heart failure, which include a central body adapted to allow the passage of interatrial blood, an anchor fixed to the central body adapted to keep the endoluminal device in place inside a defect present in the atrial partition of a patient’s heart, and a control element rotationally engaged with the central body. The rotation of the control element in relation to the central body creates a bidirectional flow of interatrial blood which allows to reduce high pressure in the right and left parts of the heart. This solution has a valve which, depending on the rotating position of a diaphragm, which position has been previously fixed, allows a flow of blood. This valve is made with a central body shutter, the rigidity of which allows the central body to maintain a certain radial force outward, against the walls of the partition, thus reducing the risk of displacement or migration of the endoluminal device.

These solutions, although being advantageous in some aspects, are very complex to implement, and especially do not allow to substantially completely occlude the partition defect while choosing freely the crossing point or re-crossing point in different positions of the diaphragm, thus facilitating the approach of the surgical device to the surgery area which can be located very differently from patient to patient and from disease to disease.

Therefore, the need for an occluding device which is simple to manufacture, easy to apply, and flexible to use after implantation for crossing the defect or the now-occluded opening of the partition in case of subsequent surgery is still strongly felt.

SUMMARY OF THE INVENTION

Therefore, it is the object of the present invention to provide a crossable interseptal occluder device, having structural and functional features that meet the aforementioned needs and overcome the drawbacks mentioned with reference to the devices of the prior art.

Some advantageous embodiments are also described.

BRIEF DESCRIPTION OF THE DRAWINGS

Further features and advantages of the present invention will become apparent from the description provided hereinafter of preferred exemplary embodiments thereof, given by way of non-limiting example, with reference to the accompanying drawings, in which.

DETAILED DESCRIPTION

Figure 1:
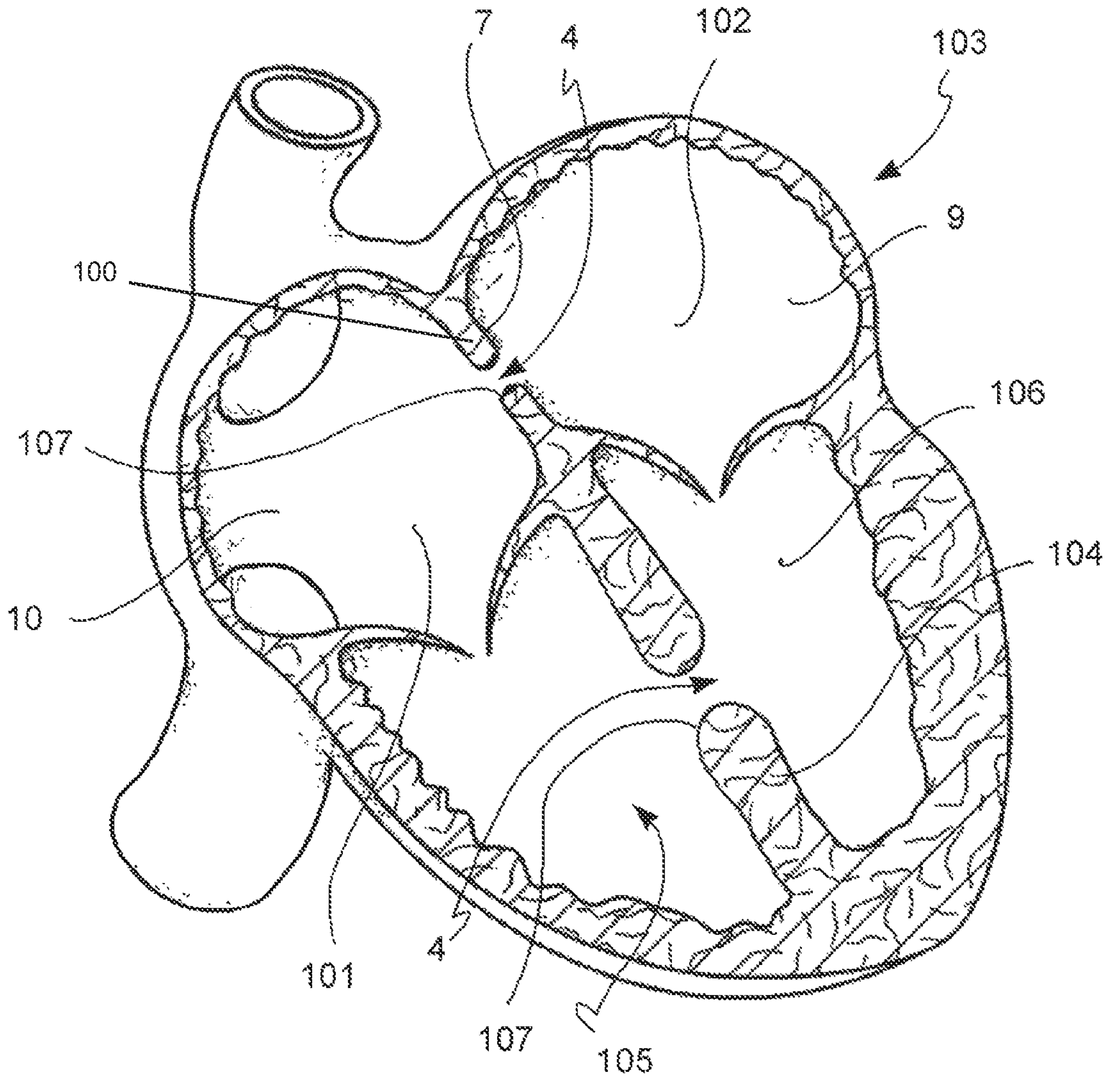
FIG. 1 is a diagrammatic sectional view of a heart in which defects or openings are present in the atrial and ventricular partitions.
Figure 2:
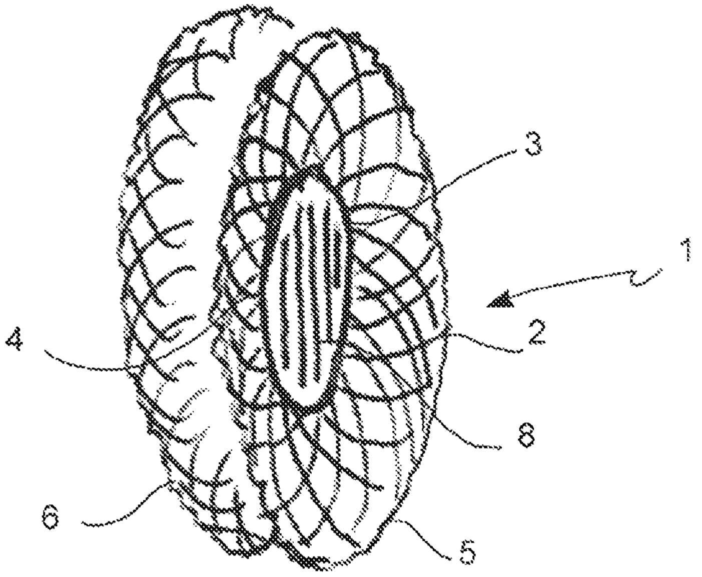
FIG. 2 shows an axonometric view of a crossable interseptal occluding device according to the present invention.
Figure 3:
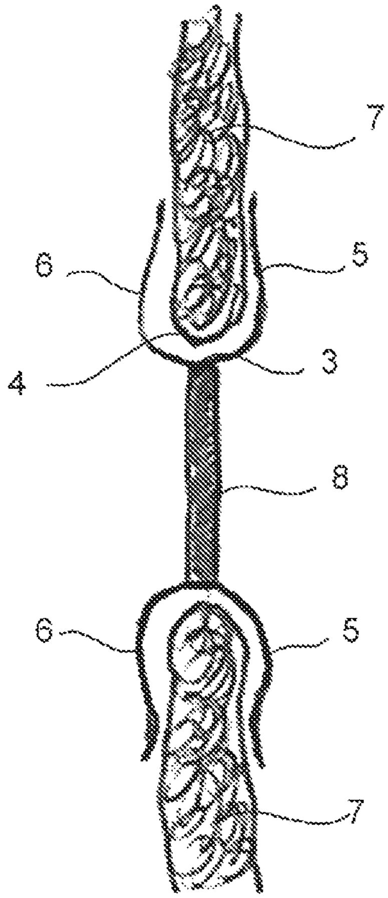
FIG. 3 is a cross-sectional view of a crossable interseptal occluding device applied to close a defect or opening of a partition.
Figure 4A:
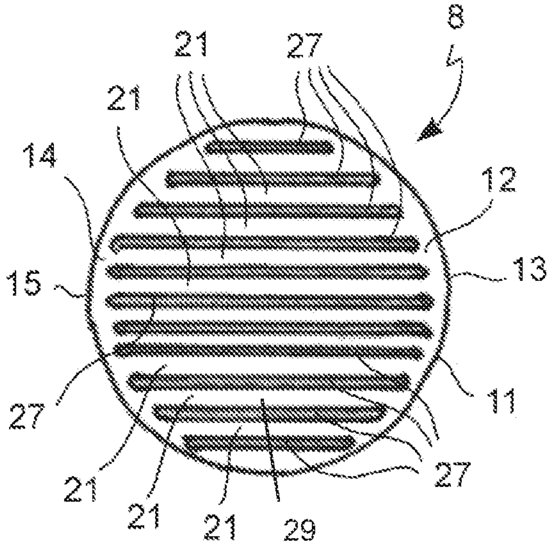
FIG. 4A is a diagrammatic front view of only the part of the diaphragm of a crossable interseptal occluding device, made according to an embodiment with parallel fringes.
Figure 4B:
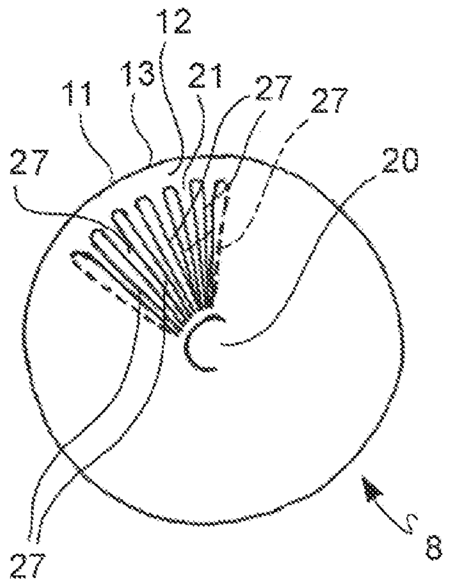
FIG. 4B is a diagrammatic front view of only the part of the diaphragm of a crossable interseptal occluding device, made according to an embodiment with radial fringes.

In accordance with a general embodiment, there is provided a crossable interseptal occluder device 1 comprising a support structure 2 in which the support structure 2 comprises a central support structure portion 3 which delimits a lumen 4.

The support structure 2 comprises a first anchoring portion 5 and an opposite second anchoring portion 6.

The support structure 2 is configured to expand and contract between a compressed tubular configuration for insertion through a patient's vasculature and an expanded or extended configuration in which the first and second anchoring portions 5, 6 extend radially outwards from the central support structure portion 3 to compress a partition 7 therebetween by arranging the support structure 2 astride the partition 7 through a defect or hole or opening present in the partition 7.

The crossable interseptal occluder device 1 further comprises at least one diaphragm 8.

The diaphragm 8 is supported by the support structure 2 and arranged to close the majority of the lumen 4, when the diaphragm 8 is in a relaxed configuration with the supporting structure 2 being extended.

The diaphragm 8 is configured to allow a medical device inserted into a first compartment 9 or 10 delimited by the partition 7 to pass through the diaphragm 8 and then through the lumen 4 entering a second compartment 10 or 9 delimited by the partition 7.

The diaphragm 8 comprises a diaphragm edge 11 placed close to the central support structure portion 3 of the support structure 2.

The diaphragm 8 comprises a plurality of elongated membrane occluding fringes or bridges 21 or occluding bridges 21.

Each of said occluding bridges 21 comprises an elongated body 50 having opposite elongated body ends or ends 51, 52 and opposite longitudinal edges or sides 22.

In a relaxed configuration of the diaphragm 8, each occluding bridge 21 of said plurality of occluding bridges 21 is arranged close to at least a further occluding bridge 21 of said plurality of occluding bridges 21.

At least one portion of the longitudinal sides 22 of each occluding bridge 21 and at least one portion of the longitudinal sides 22 of said at least a further occluding bridge 21 delimit at least one slit or cut 27 into said diaphragm 8.

Both opposite ends 51, 52 of each occluding bridge 21 are directly or indirectly connected to or supported by the support structure 2.

The term "occlude" means the possibility of minimizing or completely avoiding the flow of blood passing through the diaphragm. This definition is to describe an occlusion created by a plurality of occluding elements which, arranged to cover the lumen, create barriers while remaining at least partially independent of each other to be movable when necessary, but which tend to return, when not urged, to the occlusion position.

The term "relaxed position or configuration of the diaphragm" means a configuration both unimplanted and implanted in the patient in which the support structure is expanded or deployed or extended in which the diaphragm is not urged by external forces, but not necessarily without internal actions, such as a tension which tends to keep the occluding bridges in the occlusion position. For example, this position coincides with that of the support structure in an extended position, adapted to grasp the edges of the partition close to the edge of the lumen to be occluded. For example, but not necessarily, the relaxed position of the diaphragm coincides with an arrangement of the occluding bridges which is planar as a whole or on planes.

In accordance with an embodiment, in a relaxed configuration of the diaphragm 8, each of the longitudinal sides 22 delimits, with the side of an adjacent occluding bridge 21, an elongated and narrow opening or elongated slit 27.

In accordance with an embodiment, in a relaxed configuration of the diaphragm 8, each bridge of said plurality of occluding bridges 21 of each diaphragm 8 of said at least one diaphragm 8 lies in a single plane.

In accordance with an embodiment, in a relaxed configuration of the diaphragm 8, the plurality of occluding bridges 21 is arranged with the bridges placed side by side.

In accordance with an embodiment, in a relaxed configuration of the diaphragm 8, each occluding bridge 21 is arranged close to at least a further occluding bridge 21 facing at least one portion of a longitudinal side 22 thereof to at least one portion of a longitudinal side 22 of said further occluding bridge 21.

In accordance with an embodiment, in a relaxed configuration of the diaphragm 8, the slit or cut 27 is one elongated slit 27 or a long and narrow opening 11 delimited by occluding bridges 21.

In accordance with an embodiment, in a relaxed configuration of the diaphragm 8, each occluding bridge 21 is placed adjacent to said at least a further occluding bridge 21.

In accordance with an embodiment, in a relaxed configuration of the diaphragm 8, each of said opposite longitudinal sides 22 lies so that the sum of the elongated bodies 50 of the occluding bridges 21 occludes the majority of the lumen 4.

In accordance with an embodiment, in a relaxed configuration of the diaphragm 8, each occluding bridge 21 is arranged parallel to said at least a further occluding bridge 21.

In accordance with an embodiment, in a relaxed configuration of the diaphragm 8, the slit or cut 27 has a longitudinal extension equal to the entire longitudinal extension of the elongated body 50 of each occluding bridge 21 which delimits the slit or cut 27.

In accordance with an embodiment, in a relaxed configuration of the diaphragm 8, all slits or cuts 27 are arranged parallel to one another.

In accordance with an embodiment, except for the opposite elongated body ends 51, 52, each elongated body 50 of each occluding bridge 21 is independent of other elongated bodies 50 of other occluding bridges 21.

In accordance with an embodiment, in a relaxed configuration of the diaphragm 8, the occluding bridges 21 of said plurality of occluding bridges 21 are randomly distributed in order to occlude the majority of said lumen 4.

In accordance with an embodiment, in a relaxed configuration of the diaphragm 8, the occluding bridges 21 of said plurality of occluding bridges 21 are arranged so as to avoid from intertwining or interlacing with one another.

In accordance with an embodiment, in a relaxed configuration of the diaphragm 8, each of said bridges of said plurality of occluding bridges 21 lies in a plane arranged orthogonal to an axis of the lumen 4.

In accordance with an embodiment, in a relaxed configuration of the diaphragm 8, all bridges of said plurality of occluding bridges 21 of each diaphragm 8 lie in the same plane.

In accordance with an embodiment, both opposite ends 51, 52 of each occluding bridge 21 are directly or indirectly connected to or supported by said central support structure portion 3 of said support structure 2.

In accordance with an embodiment, the opposite longitudinal sides 22 of said plurality of occluding bridges 21 are parallel to one another.

In accordance with an embodiment, said plurality of occluding bridges 21 comprises opposite longitudinal sides 22 and said opposite longitudinal sides 22 of adjacent occluding bridges 21 are arranged side by side and in contact with one another.

In accordance with an embodiment, the diaphragm 8 is made of an elastic material, for example silicone or medical elastomer or polyurethane or bioerodible or bioabsorbable material.

In accordance with an embodiment, the diaphragm 8 is made of an elastic material capable of deformation at least between 10% and 20%.

In accordance with an embodiment, the diaphragm 8 is made of an elastic material, for example silicone or medical elastomer or polyurethane or bioerodible or bioabsorbable material; and the diaphragm 8 is made of an elastic material capable of deformation of at least 150%.

In accordance with an embodiment, the diaphragm 8 is an elastic membrane.

In accordance with an embodiment, the occluding bridges 21 of the diaphragm 8 are separated from one another in the extension thereof or central occluding bridge portion 29 but joined together in a single piece.

In accordance with an embodiment, the diaphragm edge 11 and the occluding bridges 21 are in a single piece.

In accordance with an embodiment, at least one of said occluding bridges 21 has a longitudinal extension and comprises an occluding bridge section 23 evaluated in a transverse direction to said longitudinal direction of circular shape.

In accordance with an embodiment, at least one of said occluding bridges 21 has a longitudinal extension and comprises an occluding bridge section 23 evaluated in a transverse direction to said longitudinal direction of square or rectangular shape.

In accordance with an embodiment, at least one of said occluding bridges 21 has a longitudinal extension and comprises an occluding bridge section 23 evaluated in a transverse direction to said longitudinal direction of tapered shape passing from the center of said section to a section end 24 thereof.

In accordance with an embodiment, at least one of said occluding bridges 21 has a longitudinal extension and comprises an occluding bridge section 23 evaluated in a transverse direction to said longitudinal direction of tapered shape passing from a first section base side 25 to a section end 24 thereof.

In accordance with an embodiment, at least one of said occluding bridges 21 has a longitudinal extension and comprises an occluding bridge section 23 evaluated in a transverse direction to said longitudinal direction of tapered shape passing from a first section base side 25 to smaller section side 26.

In accordance with an embodiment, at least one of said occluding bridges 21 has a longitudinal extension and comprises an occluding bridge section 23 evaluated in a transverse direction to said longitudinal direction of oval or triangular or rhomboidal or trapezoidal shape.

In accordance with an embodiment, at least one pair of said occluding bridges 21 has a longitudinal extension and comprises an occluding bridge section 23 evaluated in a transverse direction to said longitudinal direction of concave shape, in the first occluding bridge 21 of said pair, facing a convex shape, in the second occluding bridge 21 of said pair, and said concave and convex shapes are at least partially meshed with each other.

In accordance with an embodiment, at least one pair of said occluding bridges 21 has a longitudinal extension and comprises an occluding bridge section 23 evaluated in a transverse direction to said longitudinal direction of concave shape, in the first occluding bridge 21 of said pair, facing a convex shape, in the second occluding bridge 21 of said pair, and said concave and convex shapes are at least partially meshed with each other and said shapes are arched shapes.

In accordance with an embodiment, at least one pair of said occluding bridges 21 has a longitudinal extension and comprises an occluding bridge section 23 evaluated in a transverse direction to said longitudinal direction of concave shape, in the first occluding bridge 21 of said pair, facing a convex shape, in the second occluding bridge 21 of said pair, and said concave and convex shapes are at least partially meshed with each other and said shapes are triangular or trapezoidal shapes.

In accordance with an embodiment, a pair of diaphragms is included, each of the diaphragms 8 of said pair of diaphragms 28 comprising a plurality of occluding bridges 21.

The diaphragms 8 of said pair of diaphragms 28 are arranged facing each other and with the plurality of occluding bridges 21 of the first diaphragm 8 of said pair of diaphragms 28 being offset with respect to the plurality of diaphragm occluding bridges 21 of the second diaphragm 8 of said pair of diaphragms 28 by overlapping at least partially said plurality of occluding bridges 21 of the first diaphragm 8 to said plurality of elongated slits or cuts 27 of said second diaphragm 8.

In accordance with an embodiment, said plurality of occluding bridges 21 of the first diaphragm 8 has tapered occluding bridge sections 23, for example triangular or rhomboidal in shape.

The tapering of the occluding bridge sections 23 of said plurality of occluding bridges 21 of the first diaphragm 8 tapers towards said second diaphragm 8.

In accordance with an embodiment, said plurality of occluding bridges 21 of the first diaphragm 8 interpenetrates at least partially between the occluding bridges 21 of said plurality of occluding bridges 21 of the second diaphragm 8.

In accordance with an embodiment, the diaphragm 8 has a concave body or concavity facing one of the first or second compartment 9, 10.

In accordance with an embodiment, the diaphragm 8 is dome-shaped.

In accordance with an embodiment, the diaphragm 8 comprises a diaphragm stiffening structure.

In accordance with an embodiment, the diaphragm 8 comprises a diaphragm stiffening structure, the diaphragm stiffening structure comprises diaphragm ribs adapted to create a support scaffold.

In accordance with an embodiment, the diaphragm 8 comprises a diaphragm stiffening structure, the diaphragm stiffening structure comprises diaphragm ribs in a single piece with the diaphragm 8.

In accordance with an embodiment, the diaphragm 8 comprises a diaphragm stiffening structure, the diaphragm stiffening structure comprises at least one diametrical rib extending along a diameter of the diaphragm 8.

In accordance with an embodiment, the diaphragm 8 comprises a diaphragm stiffening structure, the diaphragm stiffening structure comprises at least one circumferentially extending rib.

In accordance with an embodiment, the diaphragm 8 comprises a diaphragm stiffening structure, the diaphragm stiffening structure comprises at least one radially extending rib.

In accordance with an embodiment, the diaphragm 8 comprises a diaphragm stiffening structure, the diaphragm stiffening structure comprises at least one rib extending along a circle chord.

In accordance with an embodiment, the diaphragm 8 comprises a diaphragm stiffening structure, the diaphragm stiffening structure comprises diaphragm ribs adapted to create a support frame and said at least one rib is of elastic and/or extensible shape or material.

In accordance with an embodiment, the diaphragm 8 comprises a first diaphragm portion 12 having an external continuous annular portion directly or indirectly connected to the support structure 2.

Each occluding bridge end 51, 52 is connected to the external annular diaphragm portion 12.

In accordance with an embodiment, the diaphragm 8 comprises an external annular diaphragm portion 12 directly or indirectly connected to the support structure 2.

Each occluding bridge end 51, 52 is in a single piece with the external annular diaphragm portion 12.

In accordance with an embodiment, the diaphragm 8 comprises an external annular diaphragm portion 12 directly or indirectly connected to the support structure 2.

The diaphragm 8 comprises a central disc-shaped diaphragm portion 20.

Said plurality of occluding bridges 21 is arranged radially with an external end 51 connected to the external annular diaphragm portion 12 and the internal end 52 connected to the central diaphragm disc 20.

In accordance with an embodiment, the diaphragm 8 comprises an external annular diaphragm portion 12 directly or indirectly connected to the support structure 2.

The diaphragm 8 comprises a central disc-shaped diaphragm portion 20.

Said plurality of occluding bridges 21 is arranged radially with an external end 51 connected to the external annular diaphragm portion 12 and the internal end 52 connected to the central diaphragm disc 20.

The opposite occluding bridge edges or sides 22 converge towards the central diaphragm disc 20; and each occluding bridge edge or side 22 is arranged parallel to the adjacent occluding bridge edge or side 22 of the adjacent occluding bridge 21.

In accordance with an embodiment, the diaphragm 8 comprises a plurality of hollow tubes or wires or elastic threads 42 comprising hollow tube or elastic thread stretches 41 which form the diaphragm 8.

In accordance with an embodiment, the diaphragm 8 comprises a single hollow tube or wire or elastic thread 40 folded to form hollow tube or wire or elastic thread stretches 41 which form the diaphragm 8.

In accordance with an embodiment, said plurality of hollow tubes or wires or elastic threads 42 or said single folded hollow tube or wire or elastic thread 40 is connected or folded around the support structure 2.

In accordance with an embodiment, said plurality of hollow tubes or wires or elastic threads 42 or said single folded hollow tube or wire or elastic thread 40 is connected or folded around the central support structure portion 3.

In accordance with an embodiment, the diaphragm 8 comprises a plurality of hollow tube or wire or elastic thread stretches 41 which are parallel to one another.

In accordance with an embodiment, the diaphragm 8 comprises a plurality of hollow tube or wire or elastic thread stretches 41 which are mutually arranged side by side.

In accordance with an embodiment, the diaphragm 8 comprises a plurality of hollow tube or wire or elastic thread stretches 41 which are arranged adjacent to one another.

In accordance with an embodiment, the diaphragm 8 comprises a plurality of radially arranged hollow tube or wire or elastic thread stretches 41.

In accordance with an embodiment, the diaphragm 8 comprises a first plurality of hollow tube or wire or elastic thread stretches 41 which are parallel to one another and a second plurality of hollow tube or wire or elastic thread stretches 41 which, in said second plurality, are parallel to one another but orthogonal to said first plurality of hollow tube or wire or elastic thread stretches 41.

In accordance with an embodiment, the diaphragm 8 comprises a first plurality of hollow tube or wire or elastic thread stretches 41 which are parallel to one another and at least a second plurality of hollow tube or wire or elastic thread stretches 41 which, in said at least a second plurality, are parallel to one another but inclined with respect to said first plurality of hollow tube or wire or elastic thread stretches 41.

In accordance with an embodiment, said plurality of hollow tubes or wires or elastic threads 42 or said single hollow tube or wire or elastic thread 40 is made of a superelastic material, preferably Nitinol, or silicone, or polyurethane or medical elastomer or of a bioerodable material.

In accordance with an embodiment, the crossable interseptal occluder device comprises at least two diaphragms 8.

Said at least two diaphragms 8 at least partially overlap with each other.

In accordance with an embodiment, the crossable interseptal occluder device comprises at least two diaphragms 8.

Said at least two diaphragms 8 at least partially overlap with each other so as to at least partially face at least one occluding bridge 21 of a first diaphragm 8 to at least one elongated and narrow opening or slit or cut 27 of a second diaphragm 8.

In accordance with an embodiment, the crossable interseptal occluder device comprises at least two diaphragms 8.

Said at least two diaphragms 8 at least partially overlap with each other so as to at least partially enter an elongated and narrow opening or slit or cut 27 of a second diaphragm 8 with at least one occluding bridge 21 of a first diaphragm 8, by arranging itself between two adjacent occluding bridges 21 of said second diaphragm 8.

In accordance with an embodiment, the support structure 2 is in a single piece. In accordance with an embodiment, the support structure 2 and the diaphragm 8 are in a single piece.

In accordance with an embodiment, the support structure 2 is made of medical elastomer.

In accordance with an embodiment, two diaphragms 8 are included, and the two diaphragms 8 angularly overlap with each other by arranging the occluding bridges 21 of a first diaphragm 8 crossed with respect to the occluding bridges 21 of the other diaphragm 8.

In accordance with an embodiment, two diaphragms 8 are included; and the two diaphragms 8 overlap with each other, the occluding bridges 21 of a first diaphragm 8 are arranged inclined with respect to the occluding bridges 21 of the second diaphragm 8.

In accordance with an embodiment, two diaphragms 8 are included; and the two diaphragms 8 angularly overlap with each other by arranging the occluding bridges 21 of a first diaphragm 8 so as to be orthogonal to the occluding bridges 21 of the other diaphragm 8.

In accordance with an embodiment, two diaphragms 8 are included; and the two diaphragms 8 angularly overlap with each other by arranging the occluding bridges 21 of a first diaphragm 8 at an angle between 20 degrees and 90 degrees with respect to the occluding bridges 21 of the other diaphragm 8.

In accordance with an embodiment, the crossable interseptal occluder device 1 comprises a diaphragm 8 with occluding bridges 21 in a thread; said occluding bridges 21 are mounted to a frame fixed to the support structure 2.

In accordance with an embodiment, the crossable interseptal occluder device 1 comprises a diaphragm 8 with occluding bridges 21 having a wavy occluding bridge body 50.

In accordance with an embodiment, the crossable interseptal occluder device 1 comprises a diaphragm 8 with occluding bridges 21 having a wavy occluding bridge body 50, thus allowing each wavy bridge 21 urged by a possible crossing of the diaphragm, for example by a medical device, to elongate, and then return to a closed position of the diaphragm 8.

In accordance with an embodiment, the crossable interseptal occluder device 1 comprises a diaphragm 8 with occluding bridges 21 having wavy occluding bridge edges 22, the wavy bridge edge being the side portion of the occluding bridge 21 which delimits the elongated and narrow opening or slit or cut 27, thus allowing each occluding bridge urged by a possible crossing of the diaphragm by a medical device, to elongate, and facilitating, once the device has been removed, the re-closing of the wavy bridge 21 and therefore of the diaphragm 8.

In accordance with an embodiment, in a relaxed configuration, the diaphragm 8 is planar in shape and the occluding bridges 21 are tensioned on the support structure 2.

In accordance with an embodiment, the occluding bridges 21 are slats or strips or foils or wires or hollow tubes.

In accordance with an embodiment, in a relaxed configuration of the diaphragm 8, the occluding bridges 21 are separated by slits or cuts 27 in order to avoid material continuity between one bridge and the other.

In accordance with an embodiment, in a relaxed configuration of the diaphragm 8 and when the device is not implanted in a human body, the occluding bridges 21 close the majority of the lumen 4.

In accordance with an embodiment, in a relaxed configuration of the diaphragm 8, the occluding bridges 21 cover 70-100% of the lumen 4.

In accordance with an embodiment, in a relaxed configuration of the diaphragm 8, the occluding bridges 21 are uniformly distributed over the lumen 4.

In accordance with an embodiment, in a relaxed configuration of the diaphragm 8, the occluding bridges 21 delimit slits or cuts 27 which leave free passages among the occluding bridges 21 of no more than 25% of the lumen 4.

In accordance with an embodiment, the diaphragm 8 is obtained from a single sheet where the elongated slits 27 are made by laser cutting.

In accordance with an embodiment, the diaphragm 8 is obtained from a single sheet 53 in which the elongated slits 27 are made by cuts.

Said sheet 53 is fixed to the support structure 2 crossing the lumen 4 twice.

In accordance with an embodiment, the occluding bridges 21 are concentric rings which extend along an annular path 16.

Adjacent concentric occluding bridges 21 are connected by means of radial small bridges or cut interruptions 17, 18, 19.

Said radial small bridges or cut interruptions 17, 18, 19 are circumferentially offset between three near concentric occluding bridges 21 so as to avoid a radial alignment of a plurality of radial small bridges or cut interruptions.

The sides 22 of adjacent concentric occluding bridges 21 delimit arched slits or cuts 27 aligned along a circumferential path interrupted by said radial small bridges or cut interruptions 17, 18, 19.

In accordance with an embodiment, the diaphragm 8 comprises an external continuous annular diaphragm portion 12 directly or indirectly connected to the support structure 2.

The radially outermost occluding bridge 21 is connected to the external continuous annular diaphragm portion 12 via said radial small bridges or cut interruptions 17, 18, 19.

In accordance with a general embodiment, a crossable interseptal occluder device 1 comprises a support structure 2.

Said support structure 2 comprises a central support structure portion 3 which delimits a lumen 4.

Said support structure 2 comprises a first anchoring portion 5 and an opposite second anchoring portion 6.

Said support structure 2 is configured to expand and contract between a compressed tubular configuration for insertion through the patient's vasculature and an expanded configuration in which the first and second anchoring portions 5, 6 extend radially outwards from the central support structure portion 3 to compress a partition 7 therebetween by arranging said support structure 2 astride the partition 7 through a defect or hole or opening present in the partition 7.

Said crossable interseptal occluder device 1 further comprises a diaphragm 8.

Said diaphragm 8 is supported by the support structure 2 and arranged to close at least partially the lumen 4.

Said diaphragm 8 is configured to allow a medical device inserted into a first compartment 9 or 10 delimited by the partition 7 to pass through the diaphragm 8 and then through said lumen 4 entering a second compartment 10 or 9 delimited by the partition 7.

Said diaphragm 8 comprises a diaphragm edge 11 placed close to the central support structure portion 3 of the support structure 2.

Advantageously, the diaphragm 8 comprises at least one elongated and narrow opening 27.

The term "elongated and narrow opening" means a longitudinally extending opening, predominantly with respect to the extension thereof which is transverse to said longitudinal direction.

Alternatively, the elongated and narrow opening 27 comprises one of the following embodiments:

it extends from a first diaphragm portion 12 of the diaphragm 8 placed close to a first edge stretch 13 of the diaphragm edge 11, to a second diaphragm portion 14 of the diaphragm 8 placed close to a second edge stretch 15 of the diaphragm edge 11;

or it extends from a first diaphragm portion 12 of the diaphragm 8 placed close to a first edge stretch 13 of the diaphragm edge 11, to a second diaphragm portion 14 of the diaphragm 8 placed close to a diaphragm center of the diaphragm 8;

or it extends close to the diaphragm edge 11 to cover an annular path 16 interrupted by small diaphragm bridges 17, 18, 19 which connect a central diaphragm portion 20 to the diaphragm edge 11 by forming a plurality of elongated and narrow openings 11 placed one after the other.

In accordance with an alternative embodiment, said at least one elongated and narrow opening 27 is a plurality of long and narrow openings 11 delimited by a plurality of elongated membrane fringes 21, or membrane fringes 21 or occluding bridges 21.

In accordance with an alternative embodiment, in the diaphragm 8 the multiple membrane fringes 21 are parallel to one another.

In accordance with an alternative embodiment, in the diaphragm 8 the multiple membrane fringes 21 are mutually placed side by side and spaced apart from said plurality of long and narrow openings 11.

In accordance with an alternative embodiment, said plurality of membrane fringes 21 comprises membrane fringe edges 22 and the membrane fringe edges 22 of adjacent membrane fringes 21 are mutually placed side by side and in contact with one other so that said elongated and narrow opening 27 is a slit.

In accordance with an alternative embodiment, said plurality of membrane fringes 21 comprises membrane fringe edges 22 and the membrane fringe edges 22 of adjacent membrane fringes 21 are separated from one another so that said elongated and narrow opening 27 is a free opening.

In accordance with an alternative embodiment, the diaphragm 8 is made of an elastic material, for example silicone or medical elastomer or polyurethane or of a bioerodable material.

In accordance with an alternative embodiment, the diaphragm 8 is a membrane.

In accordance with an alternative embodiment, the diaphragm 8 is an elastic membrane.

In accordance with an alternative embodiment, the membrane fringes 21 of the diaphragm 8 are separated from one another in the extension thereof or central fringe portion 29 but joined together in a single piece.

In accordance with an alternative embodiment, the diaphragm edge 11 and the membrane fringes 21 are in a single piece.

In accordance with an alternative embodiment, each of said membrane fringes 21 has a longitudinal extension and comprises a fringe section 23 evaluated in a transverse direction to said longitudinal direction of square or rectangular shape.

In accordance with an alternative embodiment, each of said membrane fringes 21 has a longitudinal extension and comprises a fringe section 23 evaluated in a transverse direction to said longitudinal direction of tapered shape passing from the center of said section to a section end 24 thereof.

In accordance with an alternative embodiment, each of said membrane fringes 21 has a longitudinal extension and comprises a fringe section 23 evaluated in a transverse direction to said longitudinal direction of tapered shape passing from a first section base side 25 to a section end 24.

In accordance with an alternative embodiment, each of said membrane fringes 21 has a longitudinal extension and comprises a fringe section 23 evaluated in a transverse direction to said longitudinal direction of tapered shape passing from a first section base side 25 to a smaller section side 26.

In accordance with an alternative embodiment, each of said membrane fringes 21 has a longitudinal extension and comprises a fringe section 23 evaluated in a transverse direction to said longitudinal direction of oval or triangular or rhomboidal or trapezoidal shape.

In accordance with an alternative embodiment, a pair of diaphragms 28 is included, each of said diaphragms 8 of said pair of diaphragms 28 comprising a plurality of membrane fringes 21 which delimit a plurality of elongated and narrow openings 27.

The diaphragms 8 of said pair of diaphragms 28 are arranged facing each other and with the plurality of membrane fringes 21 of the first diaphragm 8 of said pair of diaphragms being offset with respect to the plurality of membrane fringes 21 of the second diaphragm 8 of said pair of diaphragms 28 by overlapping at least partially said plurality of membrane fringes 21 of the first diaphragm 8 to said plurality of elongated and narrow openings 27 of said second diaphragm 8.

In accordance with an alternative embodiment, said plurality of membrane fringes 21 of the first diaphragm 8 has tapered fringe sections 23.

In accordance with an alternative embodiment, said plurality of membrane fringes 21 of the first diaphragm 8 has tapered fringe sections 23, for example with rhomboid- or triangle-shaped section.

In accordance with an alternative embodiment, the tapering of the fringe sections 23 of said plurality of membrane fringes 21 of the first diaphragm 8 tapers towards said second diaphragm 8.

In accordance with an alternative embodiment, said plurality of membrane fringes 21 of the first diaphragm 8 interpenetrates at least partially between said membrane fringes of said plurality of membrane fringes 21 of the second diaphragm 8.

In accordance with an alternative embodiment, the diaphragm 8 has a concave body or concavity facing one of the first or second compartment 9, 10.

In accordance with an alternative embodiment, the diaphragm 8 is dome-shaped.

In accordance with an alternative embodiment, the diaphragm 8 comprises a diaphragm stiffening structure.

In accordance with an alternative embodiment, the diaphragm stiffening structure comprises diaphragm ribs adapted to create a support scaffold.

In accordance with an alternative embodiment, the diaphragm stiffening structure comprises diaphragm ribs in a single piece with the diaphragm 8.

In accordance with an alternative embodiment, the diaphragm stiffening structure comprises at least one diametrical rib extending along a diameter of the diaphragm 8.

In accordance with an alternative embodiment, the diaphragm stiffening structure comprises at least one circumferentially extending rib.

In accordance with an alternative embodiment, the diaphragm stiffening structure comprises at least one radially extending rib.

In accordance with an embodiment, said at least one radially extending rib is made of an extendable, i.e. stretchable, elastic material.

In accordance with an alternative embodiment, the diaphragm stiffening structure comprises at least one rib extending along a circle chord.

In accordance with an embodiment, said at least one rib extending along a circle chord is made of an extendable, i.e. stretchable, elastic material.

In accordance with an alternative embodiment, the diaphragm 8 comprises at least one diaphragm portion shaped as a diaphragm half-dome, where said diaphragm half-dome is separated from one diametrical rib of one diaphragm stiffening structure by an elongated and narrow opening 27 shaped as an arch.

In accordance with an alternative embodiment, said elongated and narrow opening 27 shaped as an arch extends from a first diaphragm portion 12 of said diaphragm 8 placed close to a first edge stretch 13 of said diaphragm edge 11, to a second diaphragm portion 14 of said diaphragm 8 placed close to a second edge stretch 15 of said diaphragm edge 11.

In accordance with an alternative embodiment, the diaphragm 8 comprises two diaphragm portions shaped as a diaphragm half-dome, where said diaphragm half-domes are mutually placed side by side to form a diaphragm dome 39 and each of said diaphragm half-domes is separated from a diametrical rib of a diaphragm stiffening structure by an elongated and narrow opening 27 shaped as an arch.

In accordance with an alternative embodiment, said elongated and narrow opening 27 shaped as an arch of each of said two diaphragm half-domes extends from a first diaphragm portion 12 of said diaphragm 8 placed close to a first edge stretch 13 of said diaphragm edge 11, to a second diaphragm portion 14 of said diaphragm 8 placed close to a second edge stretch 15 of said diaphragm edge 11.

In accordance with an alternative embodiment, the diaphragm 8 comprises a plurality of elastic threads 42 comprising elastic thread stretches 41 which form the diaphragm 8.

In accordance with an alternative embodiment, the diaphragm 8 comprises a single elastic thread 40 folded to form elastic thread stretches 41 which form the diaphragm 8.

In accordance with an alternative embodiment, said plurality of elastic threads 42 or said single folded elastic thread 40 is connected or folded around the support structure 2.

In accordance with an alternative embodiment, said plurality of elastic threads 42 or said single folded elastic thread 40 is connected or folded around the central support structure portion 3.

In accordance with an alternative embodiment, the diaphragm 8 comprises a plurality of elastic thread stretches 41 which are parallel to one another.

In accordance with an alternative embodiment, the diaphragm 8 comprises a plurality of elastic thread stretches 41 which are mutually arranged side by side.

In accordance with an alternative embodiment, the diaphragm 8 comprises a plurality of elastic thread stretches 41 which are arranged adjacent to one another.

In accordance with an alternative embodiment, the diaphragm 8 comprises a plurality of radially arranged elastic thread stretches 41.

In accordance with an alternative embodiment, the diaphragm 8 comprises a first plurality of elastic thread stretches 41 which are parallel to one another and a second plurality of elastic thread stretches 41 which, in said second plurality, are parallel to one another but orthogonal to said first plurality of elastic thread stretches 41.

In accordance with an alternative embodiment, the diaphragm 8 comprises a first plurality of elastic thread stretches 41 which are parallel to one another and at least a second plurality of elastic thread stretches 41 which, in said at least a second plurality, are parallel to one another but inclined with respect to said first plurality of elastic thread stretches 41.

In accordance with an alternative embodiment, said plurality of elastic threads 42 or said single elastic thread 40 is made of a superelastic material, preferably Nitinol, or silicone, or polyurethane or medical elastomer or of a bioerodable material.

In accordance with an alternative embodiment, the crossable interseptal occluder device comprises at least two diaphragms 8.

In accordance with an alternative embodiment, said at least two diaphragms 8 at least partially overlap with each other.

In accordance with an alternative embodiment, said at least two diaphragms 8 at least partially overlap with each other so as to at least partially face a membrane fringe 21 of a first diaphragm 8 to an elongated and narrow opening 27 of a second diaphragm 8.

In accordance with an alternative embodiment, said at least two diaphragms 8 at least partially overlap with each other so as to at least partially enter an elongated and narrow opening 27 of a second diaphragm 8 with at least one membrane fringe 21 of a first diaphragm 8, by arranging itself between two adjacent membrane fringes 21 of said second diaphragm 8.

In accordance with an alternative embodiment, the support structure 2 is in a single piece.

In accordance with an alternative embodiment, the support structure 2 and said diaphragm 8 are in a single piece.

In accordance with an alternative embodiment, the support structure 2 is made of medical elastomer.

Those skilled in the art can make several changes and adaptations to the embodiments described above, and replace elements with others which are functionally equivalent, in order to meet contingent and specific needs, without however departing from the scope of the following claims.

Some exemplary embodiments of the present invention will be described below.

In accordance with an embodiment, the crossable interseptal occluder device 1 is made to be implanted by means of minimally invasive or percutaneous techniques.

One of the peculiarities of the crossable interseptal occluder device 1 consists in the possibility of being crossed again after some time from its implantation, in order to start new interseptal procedures.

In accordance with an embodiment, the architecture of the crossable interseptal occluder device 1 is based on two components or parts:

- a frame, or support structure 2, dedicated to the positioning and anchoring in situ of the device, generally toroidal in shape with opposing "umbrellas" or "donuts", positioned astride the defect or hole or opening, with the umbrellas or donuts arranged on opposite sides of the partition 100;
- a diaphragm 8, for example a central diaphragm, dedicated to the occlusion of the defect/hole, for example an iatrogenic or congenital defect/hole 107, with the possibility of being crossed again after some time.

The support structure 2 can be identified among those currently used or in any case described in the prior art, or it can be conceived and implemented according to an embodiment as previously described here.

From the construction point of view, for example, two main types of solutions can be referred to:

- support structure 2 obtained by means of techniques of braiding metal wires made of superelastic alloy (e.g. Nitinol; CoCr);
- support structure 2 obtained from a laser-cut and then shaped metal tube made of superelastic alloy.

For the diaphragm 8, or occluding diaphragm, some exemplary embodiments are described below.

1) Diaphragm 8 with Occluding Bridges in an "Elastic Fringe Curtain"

This diaphragm 8 consists of thin strips (fringes 21) of elastic and highly extendable material. The fringes 21 are parallel and adjacent to one another, or with a small gap to space them apart, or arranged in a sunburst pattern, or according to other construction schemes. The diaphragm 8 can also consist of one or more layers of variously crossed fringes 21. Upon crossing by the catheter, the fringes 21 move apart and elongate, thus allowing the re-crossing. The re-crossing point can be freely decided by the operator at any point of the diaphragm 8. Advantageously, the suggested solution for diaphragm and fringes, after the removal of the device, allows to re-close the fringes 21 and therefore the diaphragm 8 itself.

1-a) Diaphragm with Occluding Bridges in an "Elastic Fringe Curtain" in the Shape of a Thin Disc Depending on the technology adopted for the manufacture, the elastic fringes 21, and in particular the cross sections thereof, can be made in various shapes, as in the example in FIGS. 7B to 7E, 8A and 8B, and 9.

Figure 7A:
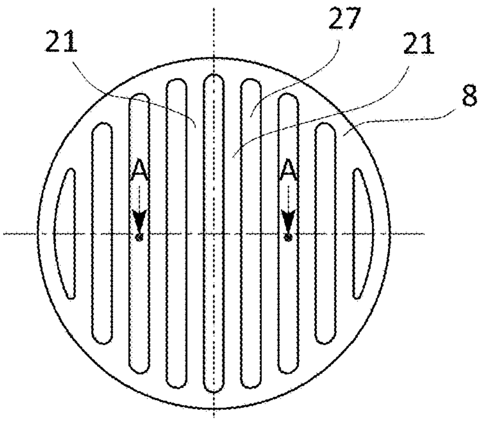
FIGS. 7A to 7E depict only the part of the diaphragm of a crossable interseptal occluding device, in a front view and in a local cross section of the fringes alone in order to show the shape of the sections of the fringes according to four different embodiments.
Figure 7B:
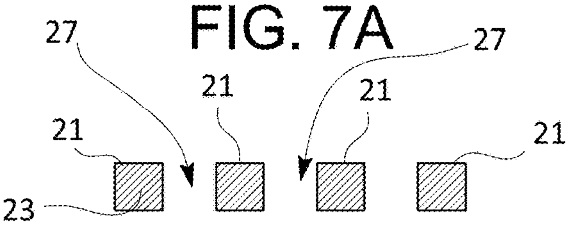
Figure 7C:
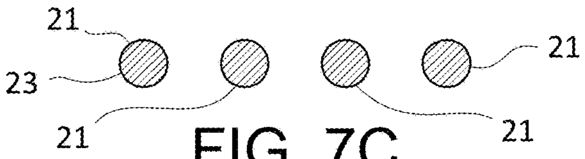
Figure 7D:
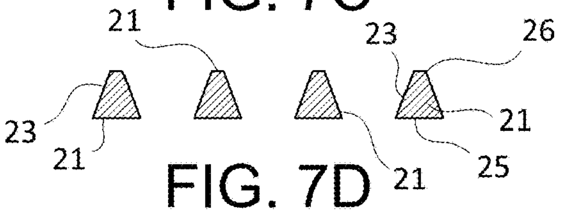
Figure 7E:
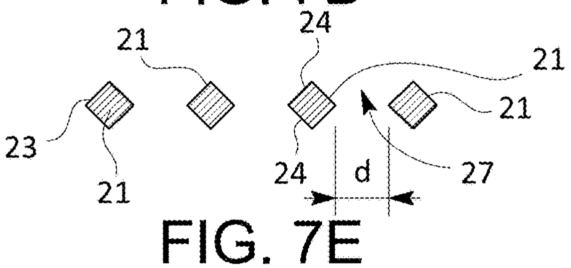

The distance "d", shown in FIG. 7E, between the fringes 21 can vary between zero (for example in diaphragms obtained from cut membranes) and a distance of the order of one millimeter. Distances of such an extent, indeed, are destined to be soon occluded by natural tissue regrowth.

The individual fringes 21 can have different shapes and orientation, and the distance therebetween may also be non-homogeneous.

In terms of materials, thin-disc diaphragms 8 can typically be made of silicone or polyurethane, choosing the types the physical-mechanical features of which are most suitable for the intended use.

In technological terms, the diaphragms 8 with elastic fringes 21 can be obtained:

- from membranes then incised in the form of a fringe;
- by molding;
- by means of 3-D printing processes;
- by means of subsequent operations of gluing various components.

The diaphragm 8 in the shape of a thin disc can also be made from bioabsorbable polymers. In this case, the possibility of re-crossing will typically be obtained at the end of the bio-absorption process, due to the substantial replacement of the diaphragm 8 with the patient's natural tissue. By adopting particularly elastic bio-absorbable polymers, re-crossability will be ensured, immediately after implantation, by an operating mechanism which is similar to that of the silicone or polyurethane diaphragms (offset+elongation of fringes).

As regards fixing of the diaphragm 8, for example in the center of the support structure 2, this can be done according to one of the techniques listed here:

- gluing
- heat sealing
- stitching
- co-molding
- crimping
- interlocking
- a mixed solution among the previous ones 1-b) Diaphragm with Occluding Bridges in an "Elastic Fringe Curtain" Obtained with Elastic Threads A second embodiment for diaphragms 8 with elastic fringes 21 is that which can be obtained from elastic and highly extendable threads 40. Such a solution can be implemented ac-cording to various approaches. For example, in a first solution, the threads 40 may be applied directly to the structures of the support structure. Or, in a second example, the threads 40 may be applied to a frame, in turn mounted to the support structure.

The threads 40 may be applied so as to create different patterns: parallel, crossed, radial threads.

In terms of materials, the same materials listed for the thin diss solution, including bioerodible polymers, are suitable for the threads 40.

The threads 40 can be obtained by extrusion or other known techniques and applied to the frames or directly to the support structure 2 by:

- winding
- binding
- heat sealing
- gluing
- pinching
- other known techniques
- mixed solutions among those listed 1-c) Diaphragm with Occluding Bridges in a "Dome of Elastic Fringes"

Physiologically, pressure differences exist between the two sides of the atrial partition, which vary within the cardiac cycle. In particular, the pressure in left atrium 102 is higher than that in the right atrium 101. A constructional solution aimed at minimizing the passage of blood from the chamber, or compartment, at a higher pressure to that at a lower pressure can be that of the "dome of elastic fringes".

The solution essentially follows that of the disc of elastic fringes described in item 1-a but, instead of developing flat, it precisely develops in the shape of a dome. The dome will be mounted to the support structure with the convexity facing the higher pressure chamber. Thereby, the blood itself, at a higher pressure, will tend to compact the adjacent fringes 21 together, thus increasing the tightness of the occlusion.

As for the materials, the technologies for making the dome, and how to fix it to the frame, the same related to the disc solution described above applies.

Some exemplary embodiment of an occluding device 1 according to the present invention will be described below.

In particular, the solution described herein has an "integral solution", or in a single piece, (support structure 2+diaphragm 8) made of medical elastomer, for example silicone or polyurethane.

In general terms, the description of the device coincides with that given in the previous embodiments, taking into account that in this embodiment the support structure does not derive from known solutions made of metal alloy, but is made of medical elastomer.

The advantages of this solution compared to those already described mainly lie in the high simplicity and cost-effectiveness of the construction, as well as in a greater lightness compared to the traditional occluders obtained from metal alloys.

In FIGS. 22 to 30, the diaphragm 8 is depicted in its shape of a "curtain of elastic fringes", but it will be able to be made according to any of the solutions described above.

The general structure of the device reflects that already described, which includes:

- a support structure 2 dedicated to the positioning and anchoring in situ of the device 1, generally toroidal in shape with opposing "umbrellas" or "donuts", positioned astride the defect or hole, with the umbrellas or donuts arranged on opposite sides of the interatrial partition;
- a diaphragm 8 or central diaphragm dedicated to the occlusion of the iatrogenic or congenital defect/hole, with the possibility of being crossed again after some time.

In this case, the support structure 2 is made of medical elastomer, and is characterized by a specific design, adapted to utilize the features of that family of materials and to optimize the functionality of the device:

- compression along the ridge;
- convexity facing the atrial chamber.

The support structure 2, in accordance with an embodiment, has a convexity facing the atrial chambers. This peculiarity offers a range of advantages:

- a gap is created between the support structure and the interatrial partition. In this gap, the tissue of the atrial partition comes out during the expansion and in-situ release of the device. In fact, it must be considered that the iatrogenic or congenital defect or hole to be occluded will have a typically smaller diameter than that of the occluder, and an irregular shape. Under the radial thrust of the occluder, the excess tissue will widen and deform, and will be accommodated in the gap provided between the anchoring portions. In the absence of this gap, the excess tissue could hinder the regular expansion of the occluder device 1;
- due to the shape provided, the support structure 2 rests on the interatrial partition mainly along the external edge only, concentrating along such an edge the compression force which stabilizes the device 1 in place. Thereby, the contact pressure is high, and the adhesion of the support structure 2 to the partition is optimal.

The above effects can be modulated by acting on dimensions and other measures as shown in FIGS. 23 to 26.

In particular, the thickening of the edge (FIG. 24), or the inclusion of a reinforcing material (FIG. 25), can strongly increase the resistance to displacement.

Figure 28:
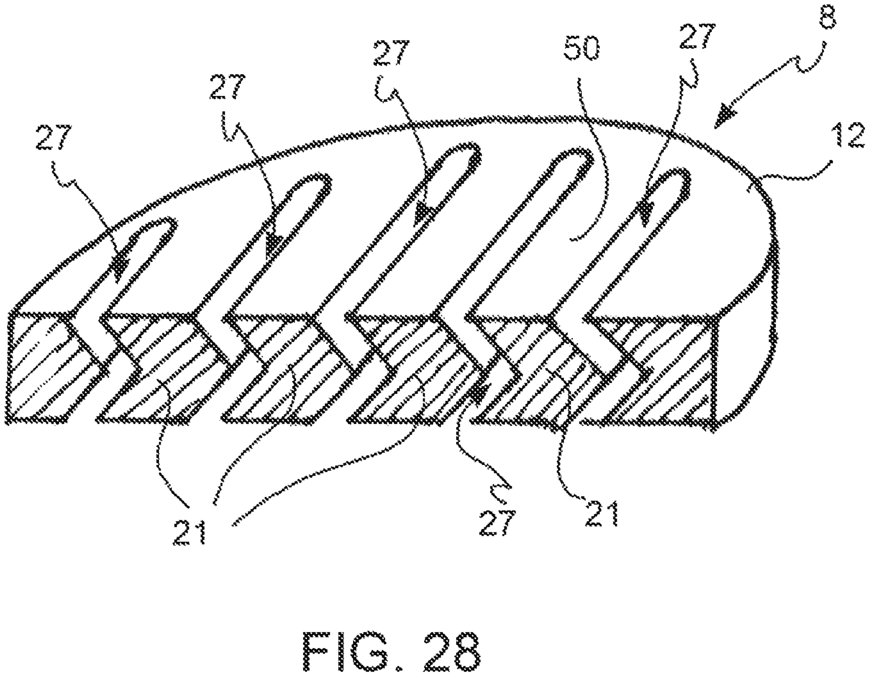
FIG. 28 shows an axonometric sectional view according to line XXVII-XXVII in FIG. 27 in which the shapes of the cross sections of the occluding bridges are highlighted, showing a meshing or geometric coupling between the different elongated bodies of the occluding bridges, thus creating slits or cuts for separating the bodies of the bridges with a winding shape.
Figure 29:
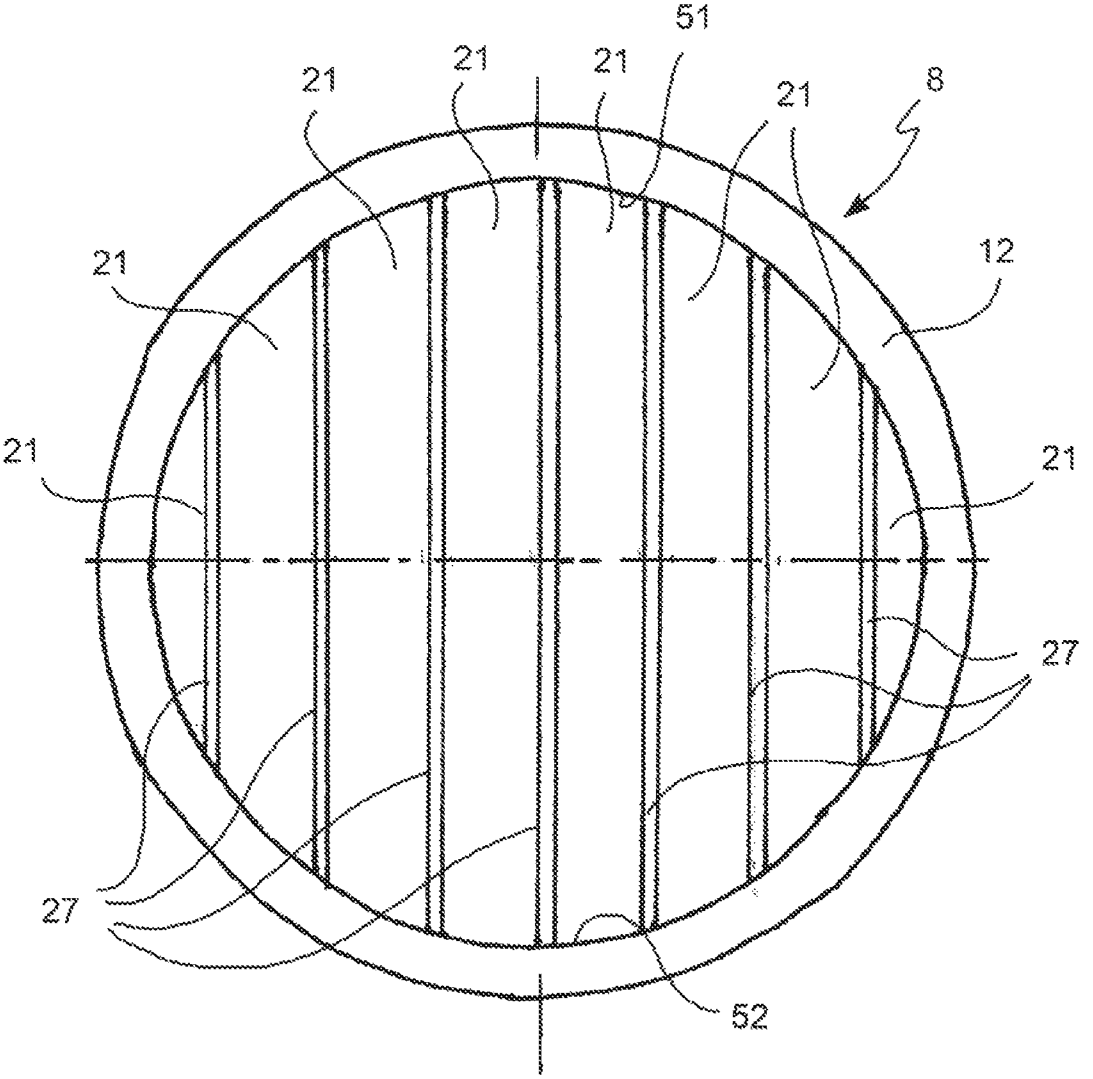
FIG. 29 is a front view of a diaphragm of a crossable interseptal occluding device, according to a further embodiment, where the occluding bridges have independent leaves in the central body portion thereof and inclined with respect to the plane of the diaphragm or lumen, so as to create winding path separation slits, for example by partially overlapping a bridge with the adjacent one.

Even in terms of the general shape of the support structure, it is possible to manufacture the device according to various solutions, according to the desired performance. For example, lobed forms for the frame umbrellas, with lobes staggered between the two sides of the partition, can facilitate the anchoring and the ease of "crimping" the device on a delivery catheter (FIGS. 28 and 29).

Figure 30:
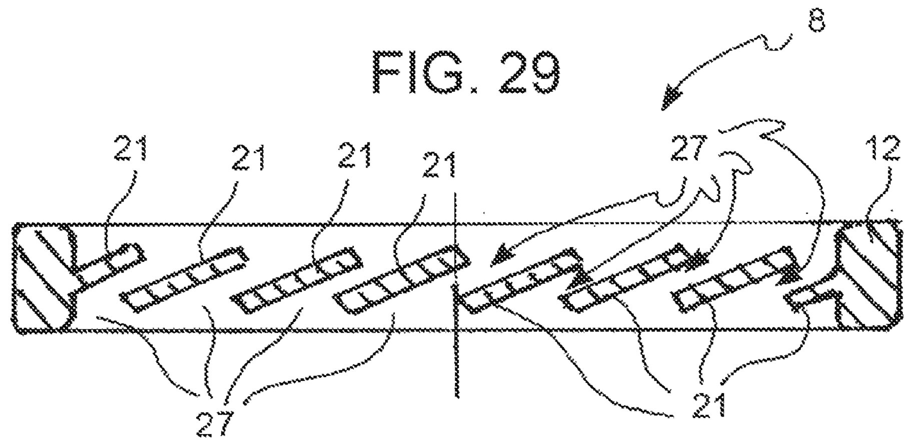
FIG. 30 shows a section according to line XXX-XXX in FIG. 29 of the diaphragm in FIG. 29.
Figure 31:
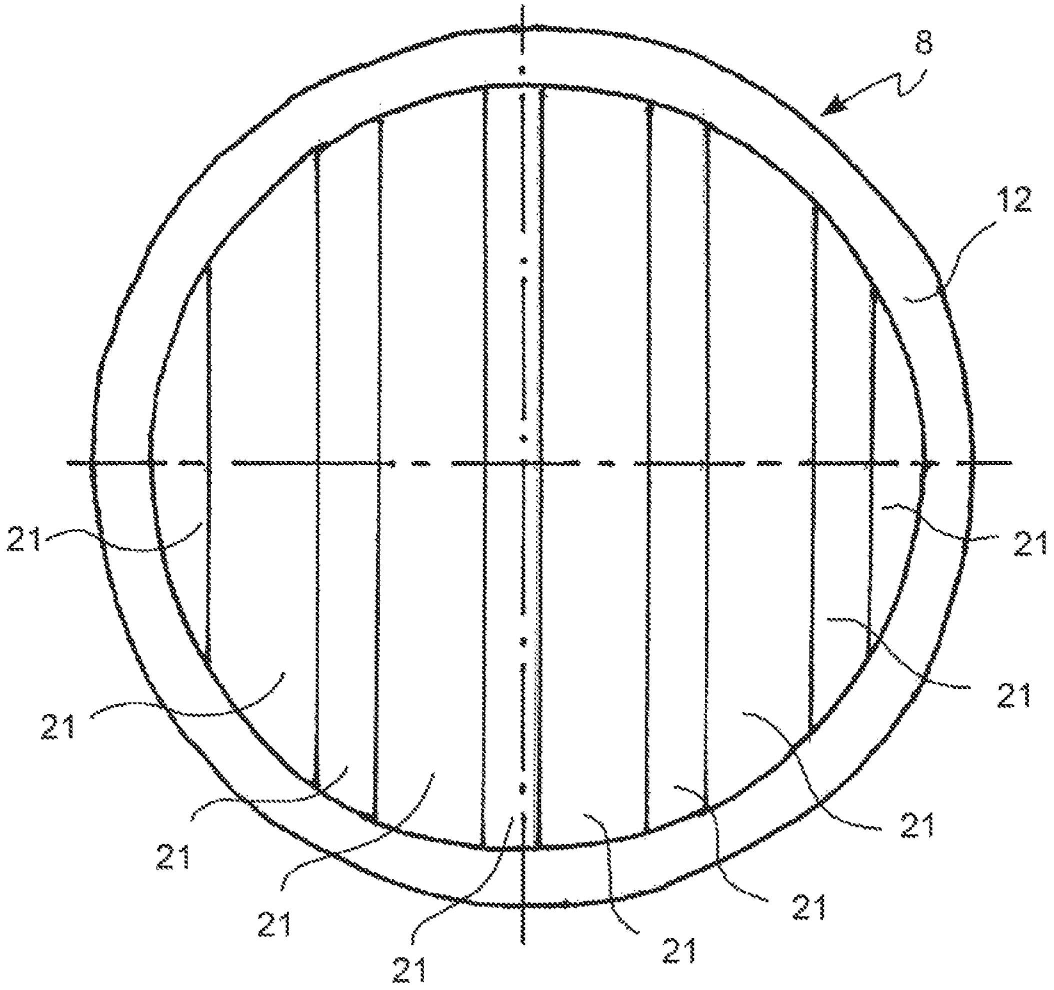
FIG. 31 is a front view of a diaphragm of a crossable interseptal occluding device, according to a further embodiment, where the occluding bridges have independent leaves in the central body portion thereof, which are arranged so as to be offset on two planes, alternatively on a first plane and on a second plane which is offset from and parallel to the first one, so as to create winding path separation slits, for example by partially overlapping a bridge with the adjacent one.
Figure 32:
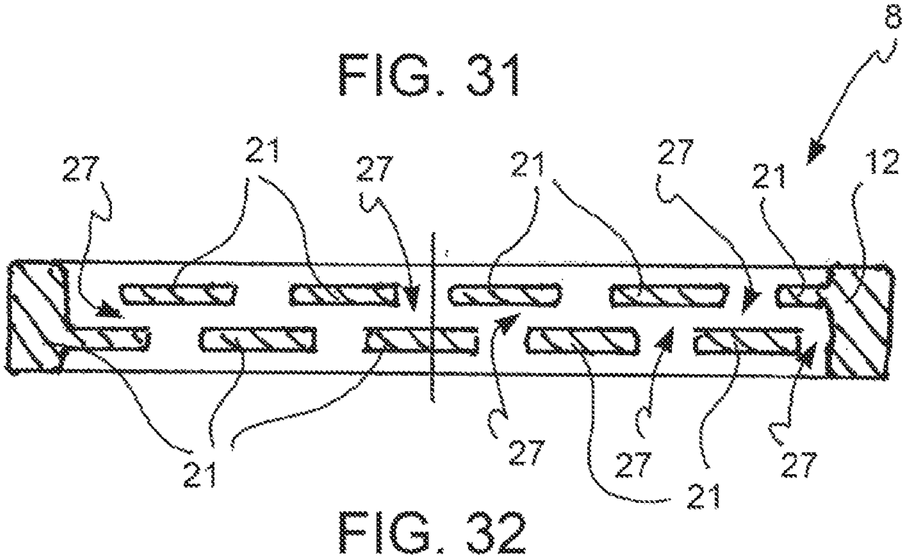
FIG. 32 shows a section according to line XXXII-XXXII in FIG. 31 of the diaphragm in FIG. 31.
Figure 33:
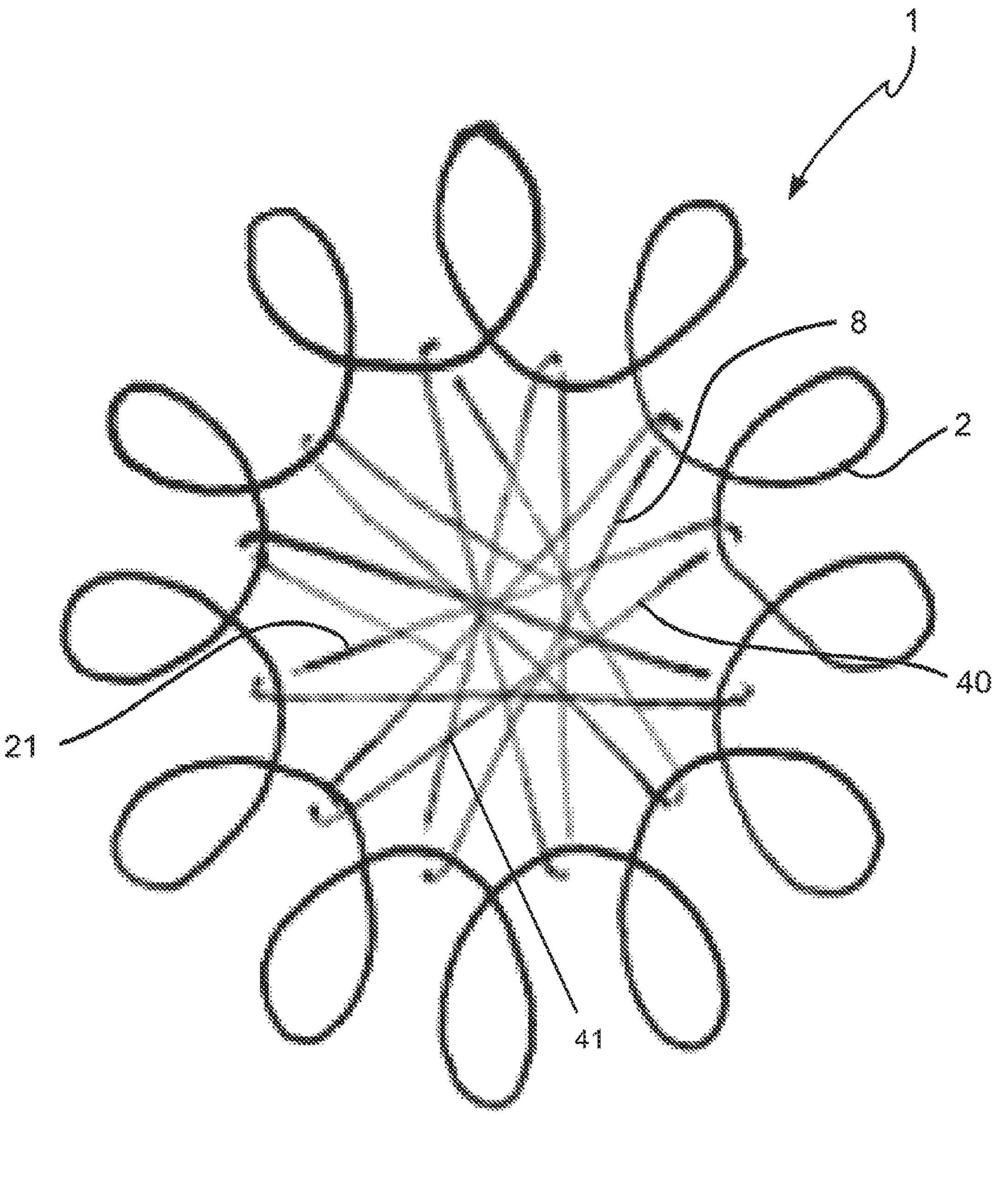
FIG. 33 is a diagrammatic view of a crossable interseptal occluding device in which the diaphragm is made from elements or a single thread-like element wrapped around the support structure, such as a tube, or an elastic thread, arranged so as to causally cross the area of the lumen and create a substantial occlusion in the majority of the lumen.

It is also possible to vary the design of the umbrellas by making cuts or openings in appropriate shapes and positions. Thereby, the device 1 is lightened, the creation of massive thrombotic formations between the umbrella and the interatrial partition is avoided, and the "crimping" of the device on the delivery catheter is facilitated (FIG. 30).

In terms of materials, the whole device 1 is made of medical elastomer, typically silicone or polyurethane. Alternatively, the whole device 1 is made of bio-erodible polymers.

The preferred solution is obtained by molding, according to known techniques, the component in a single piece.

In accordance with an embodiment, the device can also be obtained by assembling, typically by gluing, parts obtained with elastomers which are different in hardness or elasticity. For example, the support structure 2 could be made of a single piece of more rigid elastomer, by applying a more pliable elastomer diaphragm 8 in the center.

There is also the possibility of co-molding, inserting, applying other local reinforcement components, or intended for other functions, made of different materials: metallic alloys, polymer threads, fabrics, and the like.

Figures 8A, 8B:
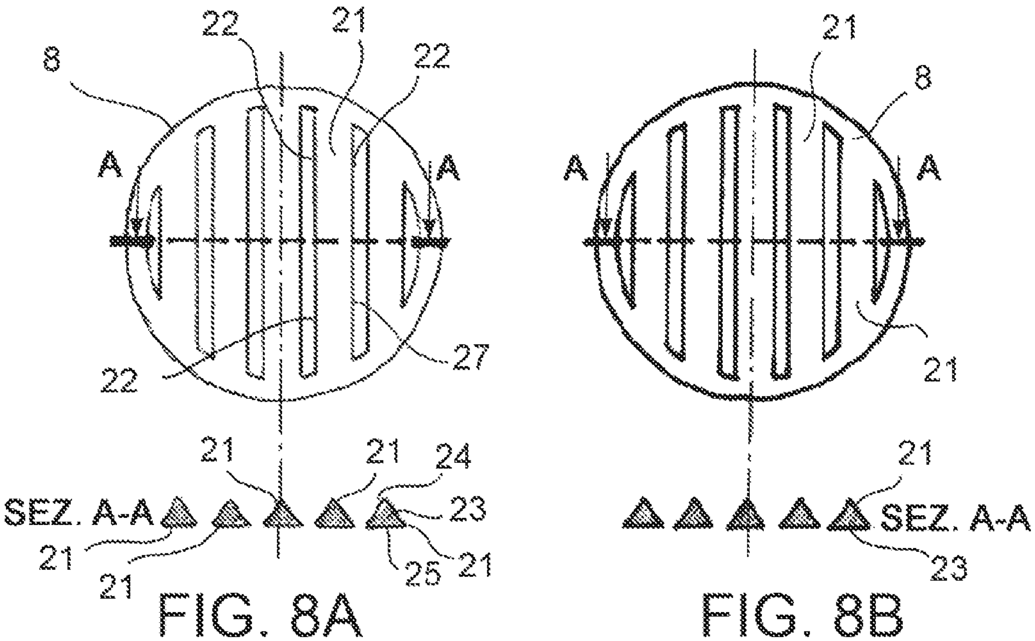
FIGS. 8A and 8B show only the part of the diaphragm of a crossable interseptal occluding device, in a front view and in a local cross section of the fringes alone according to an embodiment with tapered fringes.
Figure 9:
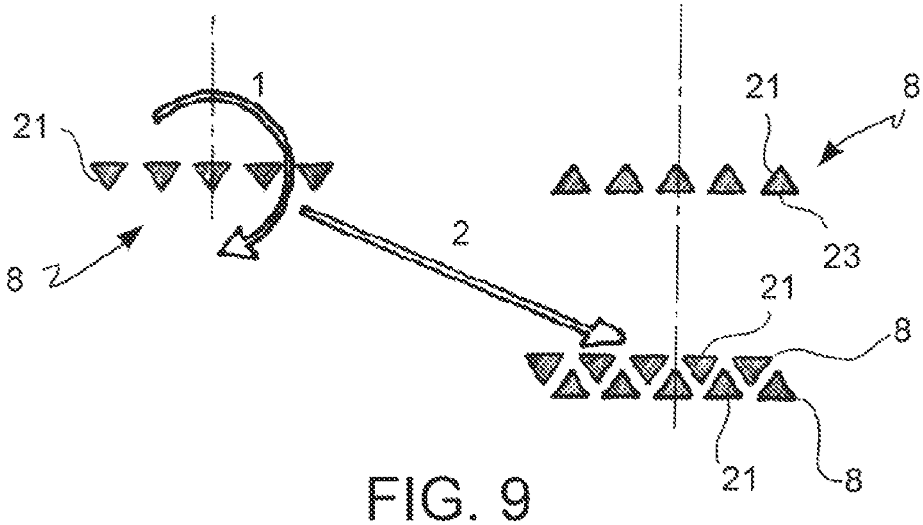
FIG. 9 depicts only the local cross sections of two diaphragms with tapered fringes, in a facing phase, in which one diaphragm is rotated and offset from the second one, so as to arrange the tapered fringes thereof between the tapered fringes of the facing diaphragm and mutually partially interpenetrated.
Figure 10:
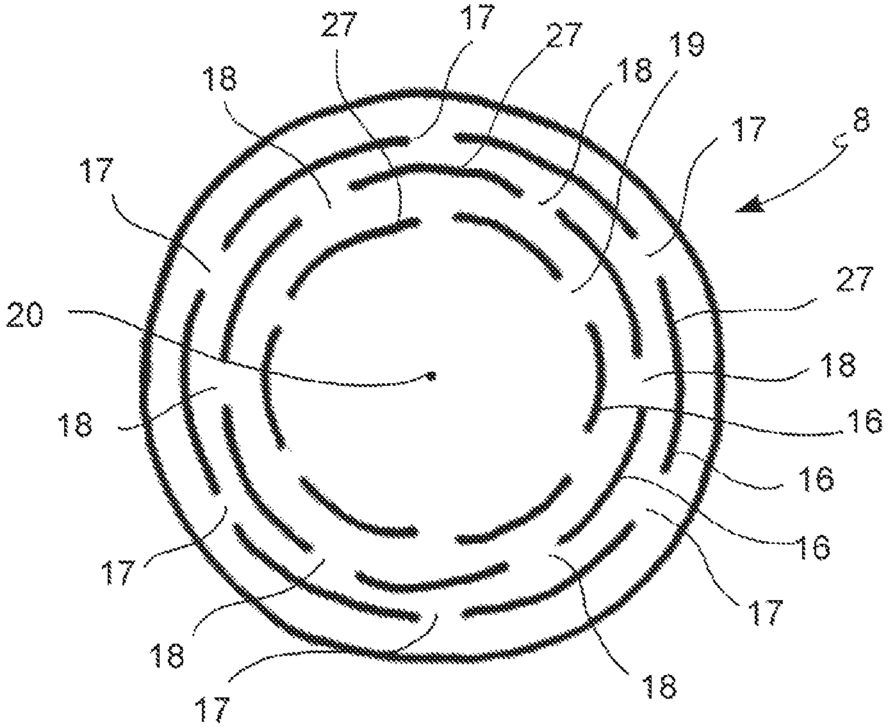
FIG. 10 is a diagrammatic front view of only the part of the diaphragm of a crossable interseptal occluding device, made according to an embodiment with radial fringes and annular path interrupted by small bridges.
Figure 11:
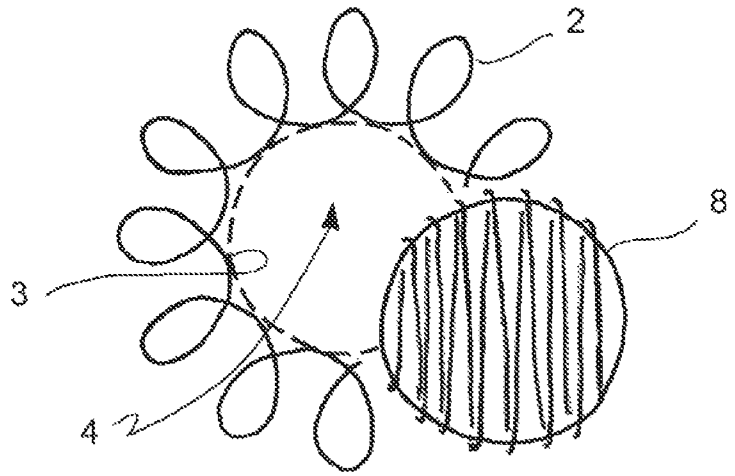
FIG. 11 is a diagrammatic front view of an operation for connecting a diaphragm to a support structure to obtain a crossable interseptal occluding device.
Figure 12:
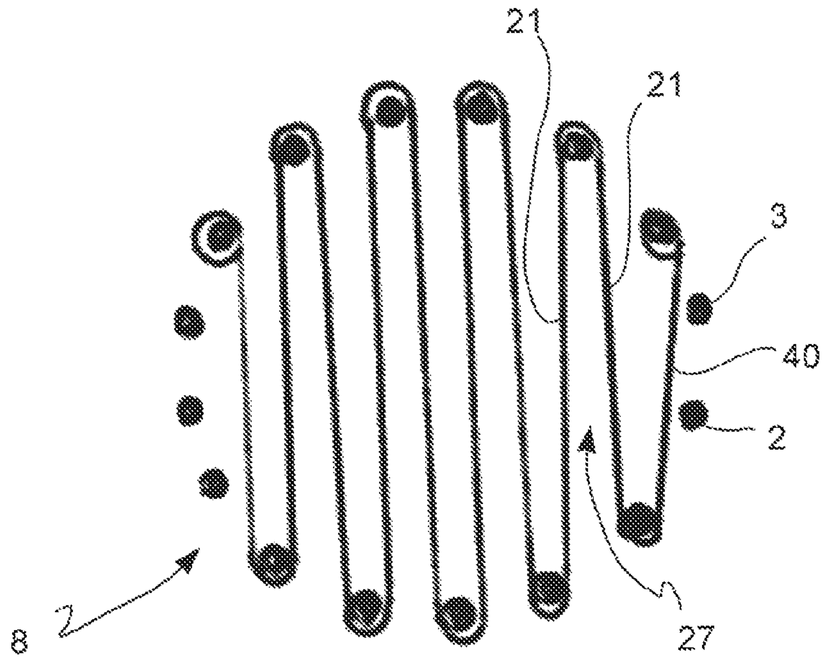
FIG. 12 depicts a diaphragm of a crossable interseptal occluding device made with a single wire folded and forming wire stretches which are mutually substantially parallel.

In accordance with an alternative embodiment, two fringed diaphragms 8 are provided, the fringes 21 of which have a tapered cross section, for example triangular or trapezoidal. Said two diaphragms 8 overlap with each other and are slightly staggered, so as to intercalate the respective fringes 21 and arrange the triangular or rhomboidal sections of either diaphragm at least partially interpenetrated to improve the fluid tightness, as shown in FIGS. 8A, 8B, 9, for example.

Figure 5:
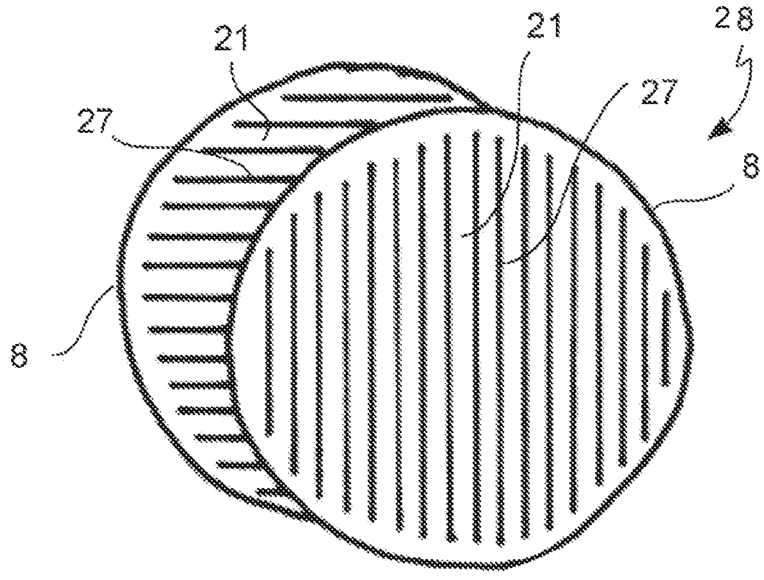
FIG. 5 is a diagrammatic front view of only the part of the diaphragm of a crossable interseptal occluding device, made according to an embodiment where two diaphragms at least partially overlap with each other and the fringes thereof, arranged parallel in the same diaphragm, are oriented orthogonal to the facing diaphragm.
Figure 6:
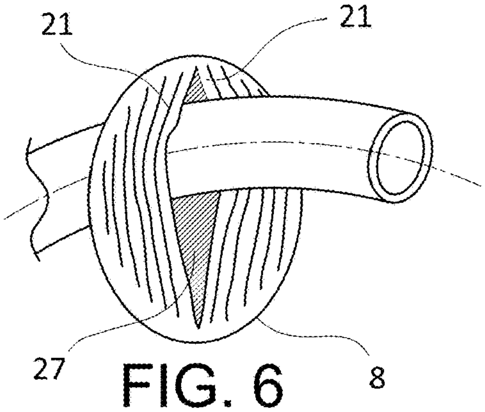
FIG. 6 is a perspective view of only the part of the diaphragm of a crossable interseptal occluding device crossed by a medical device, here depicted as a tubular body only, by moving away and extending the fringes of said diaphragm.
Figure 13:
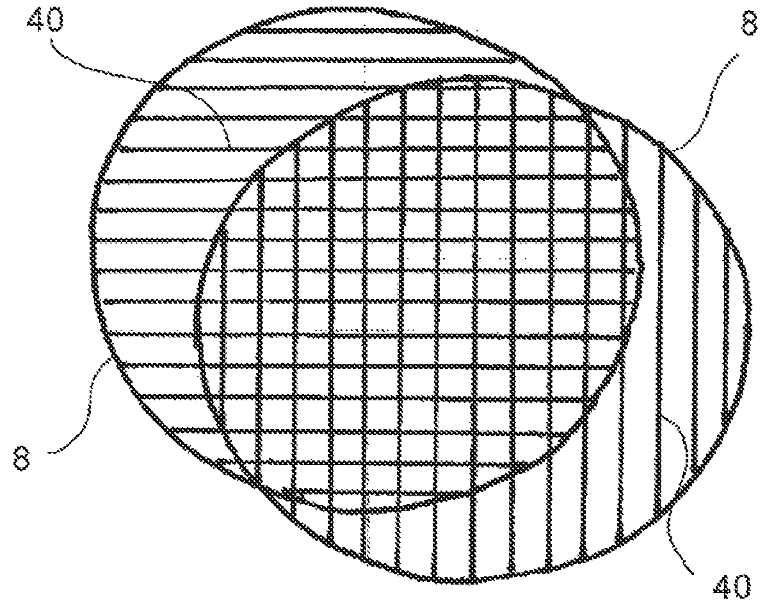
FIG. 13 is a diagrammatic front view of only the part of the diaphragm of a crossable interseptal occluding device, made according to an embodiment where two diaphragms at least partially overlap with each other and the fringes thereof, shaped as wires, are arranged parallel in the same diaphragm, but are oriented orthogonal to the facing diaphragm.
Figure 14:
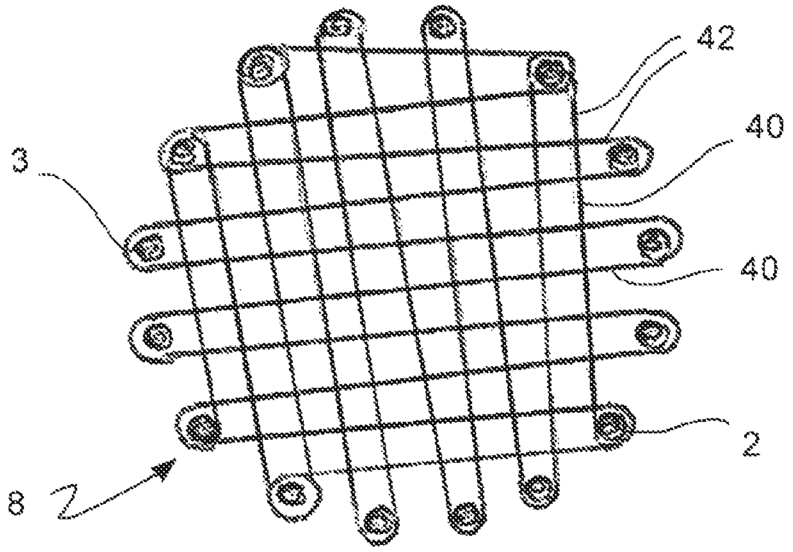
FIG. 14 depicts a diaphragm of a crossable interseptal occluding device made with wires folded and forming first wire stretches which are mutually substantially parallel and second stretches which are substantially parallel but transverse to the first stretches.
Figure 15:
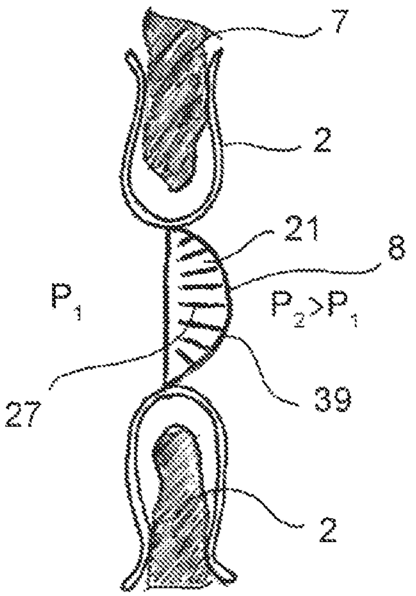
FIG. 15 is a cross-sectional view of a crossable interseptal occluding device applied to close a defect or opening of a partition, in which the diaphragm is dome-shaped with concavity facing the cavity or compartment where a higher pressure is expected.
Figure 16:
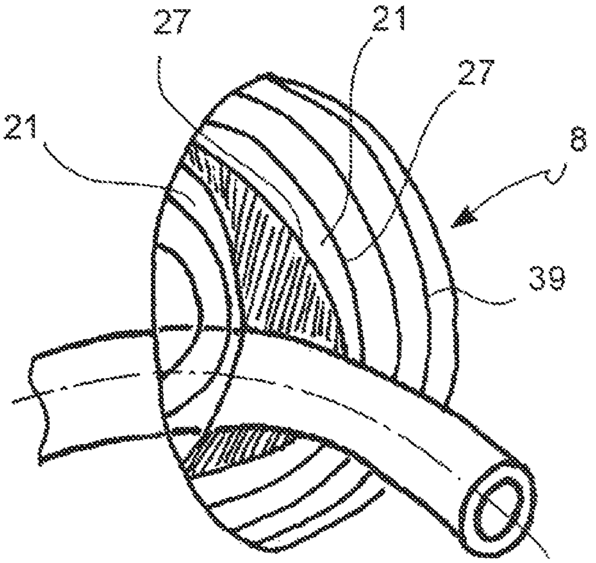
FIG. 16 is an axonometric view of a diaphragm of a crossable interseptal occluding device, in which the diaphragm is dome-shaped with concavity facing the cavity or compartment where a higher pressure is expected and is crossed by a medical device, here depicted in a tubular shape only, which moves and extends the fringes.
Figure 17:
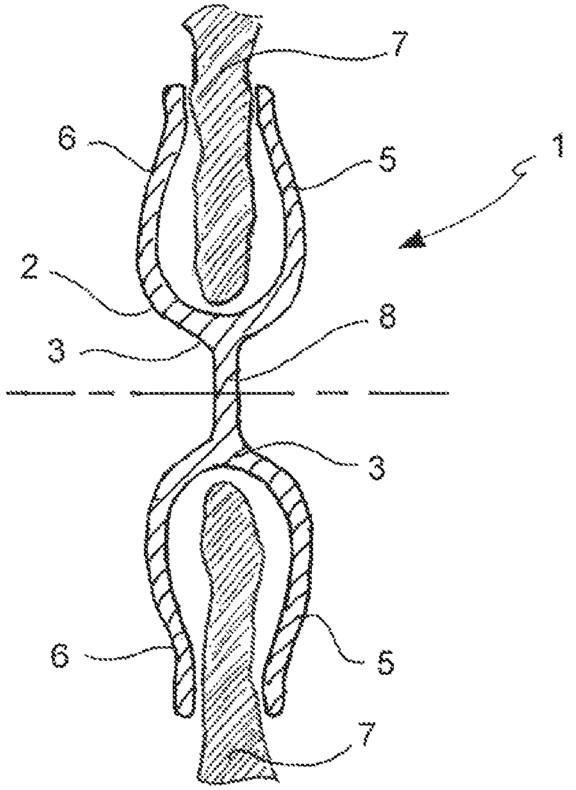
FIG. 17 shows a cross-sectional views of a crossable interseptal occluding device applied to close a defect or opening of a partition, in which the diaphragm is in one piece with the support structure anchored to the partition.
Figure 18:
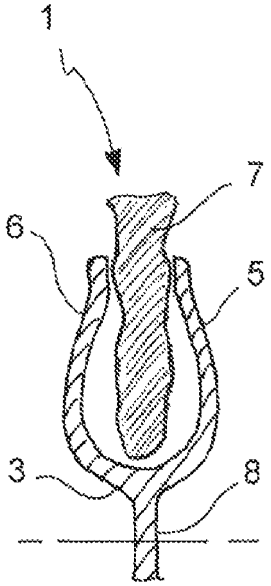
FIGS. 18 to 21 show cross-sectional views of different embodiments of the anchoring portions of a support structure applied to a defect or opening of a partition and made in a single piece with the diaphragm.
Figure 19:
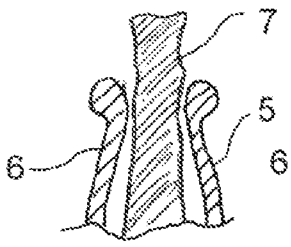
Figure 20:
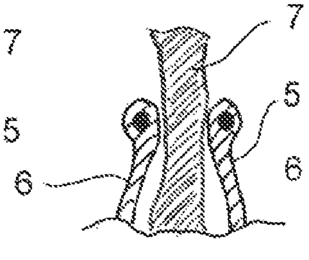
Figure 21:
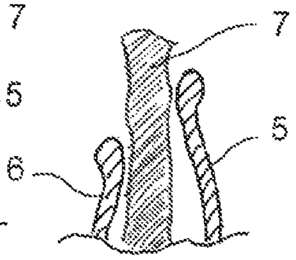
Figure 22:
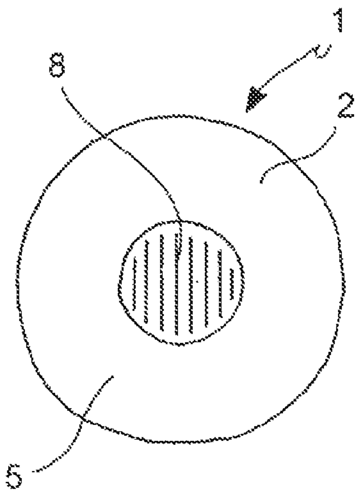
FIGS. 22 to 24 show a front view of different embodiments of anchoring portions of support structures of crossable interseptal occluding devices, in particular disc-shaped, three-lobed and angularly offset, six-lobed and angularly offset.
Figure 23:
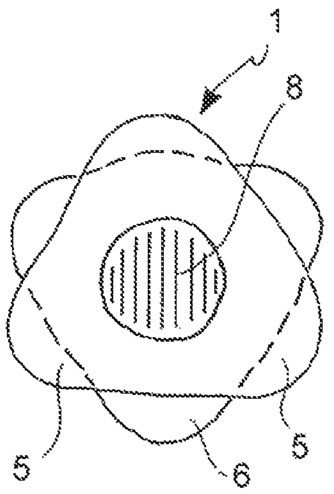
Figure 24:
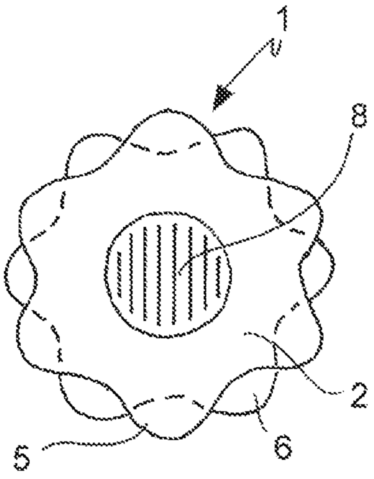
Figure 25:
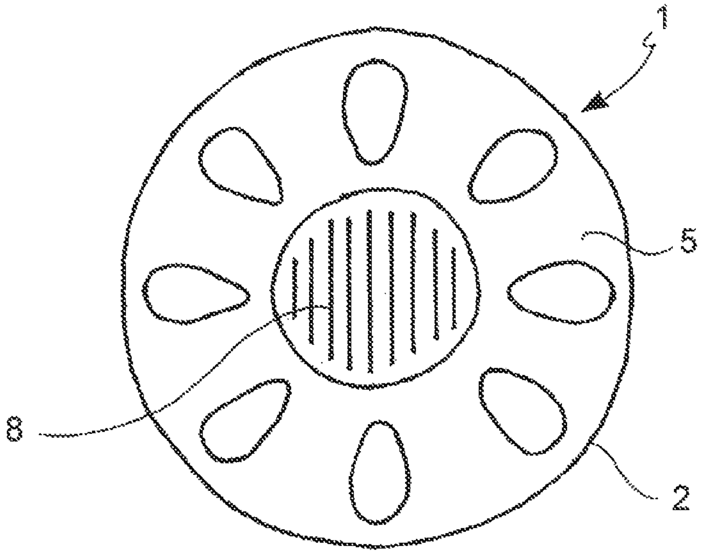
FIG. 25 is a front view of a crossable interseptal occluding device in which at least one of the anchoring portions of a support structure has circumferentially distributed openings.
Figure 26:
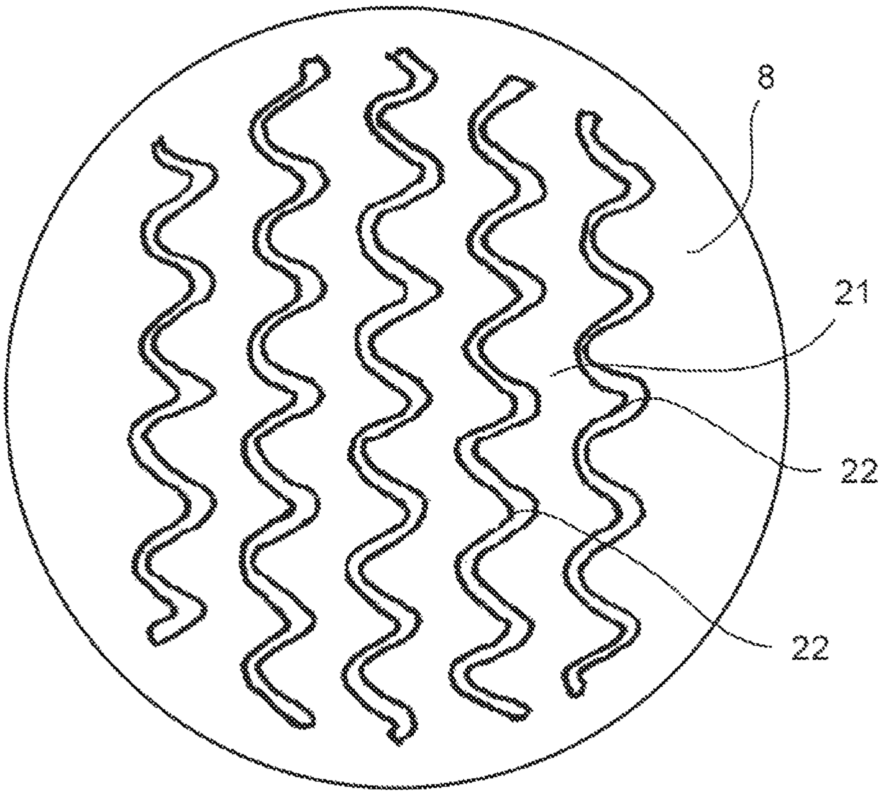
FIG. 26 shows a diagrammatic front view of only the part of the diaphragm of a crossable interseptal occluding device, made according to an embodiment with fringes and wavy fringe edges or fringes with wavy fringe body, which is suitable for a greater elastic extension in case of re-crossing by a medical device.
Figure 27:
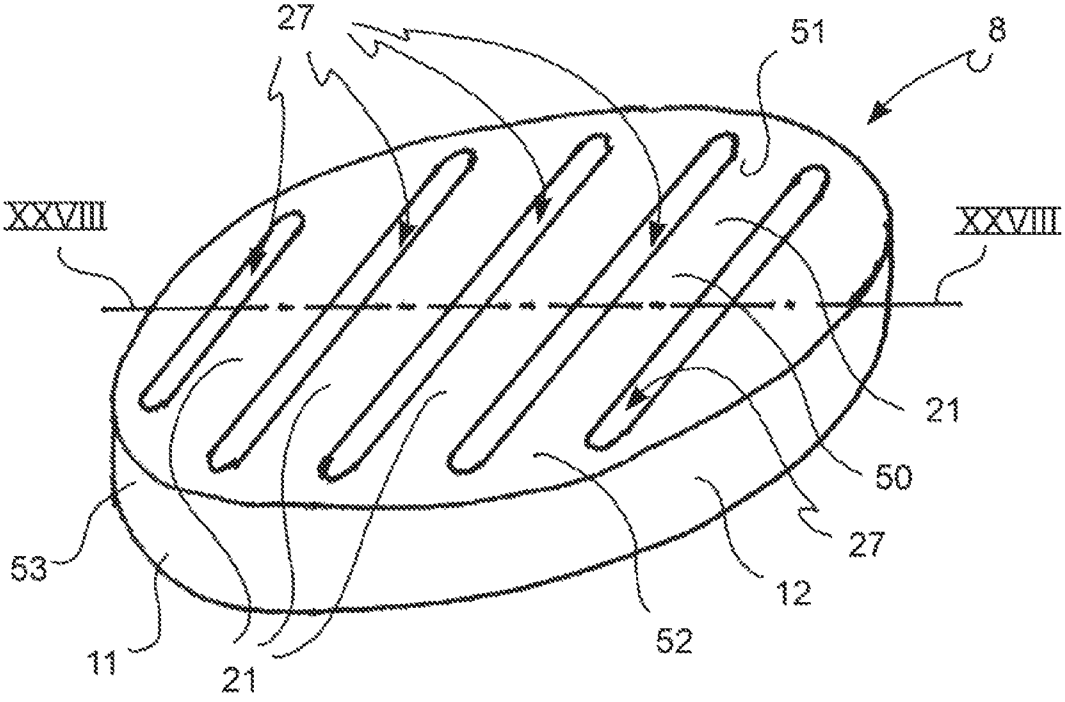
FIG. 27 is a diagrammatic axonometric view of only the diaphragm of the crossable interseptal occluding device, in which the occluding bridges are according to a further embodiment.

In accordance with an alternative embodiment, two fringed diaphragms 8 are provided. Said two fringed diaphragms 8 overlap with each other by angularly arranging the fringes 21 of a diaphragm 8 crossed with respect to the fringes 21 of the other diaphragm 8. For example, the fringes 21 of a first diaphragm 8 are arranged orthogonal to the fringes 21 of the second diaphragm 8, as shown in FIG. 5 or in FIG. 13, for example, where the fringes are in a thread.

In accordance with an alternative embodiment, a diaphragm 8 with fringes 21 in a thread is provided. Said thread-like fringes 21 are mounted to frame and said frame is fixed to said support structure 2.

In accordance with an alternative embodiment, a diaphragm 8 with fringes 21 having a wavy fringe body is provided, thus allowing each fringe urged by a possible crossing of the diaphragm, to elongate, and then return to a closed position of the diaphragm 8.

In accordance with an alternative embodiment, a diaphragm 8 with fringes 21 having wavy fringe edges is provided, the fringe edge being the lateral portion of the fringe which delimits said elongated and narrow opening 27, thus allowing each fringe urged by a possible crossing of the diaphragm by a medical device, to elongate, but facilitating, once the device has been removed, the re-closing of the fringes 21 and therefore of the diaphragm 8.

All different embodiments of diaphragm 8 and fringes 21 thereof described above advantageously allow the re-crossing of the diaphragm 8, after its implantation, and equally advantageously, after the removal of the medical device, allow the re-closing of the fringes 21 and therefore the re-closing of the diaphragm 8.

LIST OF REFERENCE NUMERALS

1 crossable interseptal occluder device
2 support structure
3 central support structure portion
4 lumen
5 first anchoring portion
6 second anchoring portion
7 partition
8 diaphragm
9 first compartment
10 second compartment
11 diaphragm edge
12 first diaphragm portion or external continuous annular diaphragm portion
13 first edge stretch
14 second diaphragm portion
15 second edge stretch
16 annular path
17 small diaphragm bridges
18 small diaphragm bridges
19 small diaphragm bridges
20 central diaphragm portion
21 elongated membrane fringes or occluding bridges
22 membrane fringe edges or occluding bridge edges or occluding bridge sides
23 fringe section or bridge section
24 section end
25 first section base side
26 smaller section side
27 elongated and narrow opening or cut
28 pair of diaphragms
29 central fringe portion or central occluding bridge portion
39 diaphragm dome
40 elastic threads or single elastic thread
41 elastic thread stretches
42 plurality of elastic threads
50 occluding bridge body
51 occluding bridge body end
52 occluding bridge body end
53 single sheet forming said diaphragm
100 atrial partition
101 right atrium
102 left atrium
103 heart
104 ventricular partition
105 right ventricle
106 left ventricle
107 defect or opening

The invention claimed is:

1. A crossable interseptal occluder device configured to be implanted within a heart of a patient, the crossable interseptal occluder device comprising:

a support structure comprising:

a central support structure portion delimiting a lumen;

a first anchoring portion comprising a first external edge; and a second anchoring portion comprising a second external edge, the second anchoring portion opposite the first anchoring portion; and said support structure being configured to contract and expand between a compressed tubular configuration for insertion through a patient's vasculature, and an expanded configuration, in which the first anchoring portion and the second anchoring portion extend radially outwards from said central support structure portion to compress a septum of the heart therebetween by arranging said support structure astride said septum through a defect or hole or opening in the septum, the septum separating a first compartment and a second compartment of the heart, wherein the first anchoring portion and the second anchoring portion are shaped to apply a compression force on the septum of the heart, wherein the compression force is concentrated between the first external edge of the first anchoring portion and the second external edge of the second anchoring portion; and a first diaphragm comprising a plurality of occluding bridges; and a second diaphragm comprising a second plurality of occluding bridges, wherein the first diaphragm and the second diaphragm are arranged facing each other and with the plurality of occluding bridges offset with respect to the second plurality of occluding bridges, wherein the first diaphragm and the second diaphragm are supported by said support structure and configured to occlude a majority of said lumen when the first diaphragm and the second diaphragm are in a relaxed configuration, wherein the first diaphragm and the second diaphragm are further configured to allow a medical device inserted into the first compartment to pass through the first diaphragm, the second diaphragm, and through said lumen to enter the second compartment, wherein the plurality of occluding bridges at least partially interpenetrate between occluding bridges of the second plurality of occluding bridges in the relaxed configuration, and wherein:

each occluding bridge of said plurality of occluding bridges comprises an elongated body having opposite elongated body ends, and opposite longitudinal edges, said opposite longitudinal edges being unconstrained such that the plurality of occluding bridges delimit a plurality of slits or cuts, the plurality of slits or cuts extending parallel to each other when the first diaphragm and the second diaphragm are in the relaxed configuration;

in the relaxed configuration, said first diaphragm is planar in shape and said plurality of occluding bridges are tensioned on said support structure;

in the relaxed configuration, each occluding bridge of said plurality of occluding bridges is disposed close to and parallel to at least one other adjacent occluding bridge of said plurality of occluding bridges;

the first diaphragm is an elastic membrane; and said plurality of occluding bridges and said second plurality of occluding bridges are configured to move away and extend to allow said medical device to pass through the first diaphragm and the second diaphragm.

2. The crossable interseptal occluder device of claim 1, wherein each slit or cut of the plurality of slits or cuts is delimited by a first longitudinal edge of a first occluding bridge and a second longitudinal edge of a second occluding bridge, said first occluding bridge adjacent to said second occluding bridge.

3. The crossable interseptal occluder device of claim 1, wherein in the relaxed configuration, each occluding bridge of said plurality of occluding bridges rests in a single plane.

4. The crossable interseptal occluder device of claim 1, wherein in the relaxed configuration, each occluding bridge is disposed close to a further occluding bridge facing with at least one portion of its longitudinal edge at least one portion of a longitudinal edge of said further occluding bridge.

5. The crossable interseptal occluder device of claim 1, wherein in the relaxed configuration, each of said opposite longitudinal edges rests in a manner that a sum of elongated bodies of said plurality of occluding bridges occludes the majority of said lumen.

6. The crossable interseptal occluder device of claim 1, wherein in the relaxed configuration, each slit or cut of the plurality of slits or cuts has a longitudinal extension equal to an entire longitudinal extension of said elongated body of each occluding bridge delimiting said slit or cut.

7. The crossable interseptal occluder device of claim 1, wherein said opposite elongated body ends of each occluding bridge are directly or indirectly connected to or supported by said central support structure portion of said support structure.

8. The crossable interseptal occluder device of claim 1, wherein the first diaphragm and the second diaphragm are made of elastic material capable of a deformation ranging from at least 10% to 20%.

9. The crossable interseptal occluder device of claim 1, wherein said plurality of occluding bridges are separated from one another in an occluding bridge extension or central portion of each occluding bridge of said plurality of occluding bridges but joined together in a single piece.

10. The crossable interseptal occluder device of claim 1, wherein:

at least one occluding bridge of said plurality of occluding bridges has a longitudinal extension and comprises an occluding bridge section evaluated in a direction transverse to a longitudinal direction of tapered shape passing from a center of said occluding bridge section to a section end thereof; or at least one occluding bridge of said plurality of occluding bridges has a longitudinal extension and comprises an occluding bridge section evaluated in a direction transverse to a longitudinal direction of tapered shape passing from a first section base side to a section end; or at least one occluding bridge of said plurality of occluding bridges has a longitudinal extension and comprises an occluding bridge section evaluated in a direction transverse to a longitudinal direction of tapered shape passing from a first section base side to a smaller section side; or at least one occluding bridge of said plurality of occluding bridges has a longitudinal extension and comprises an occluding bridge section evaluated in a direction transverse to a longitudinal direction of triangular, rhomboid, or trapezoidal shape.

11. The crossable interseptal occluder device of claim 1, wherein:

said plurality of occluding bridges have tapered occluding bridge sections being triangular or rhomboid shaped; and the tapered occluding bridge sections taper in a direction towards said second diaphragm.

12. The crossable interseptal occluder device of claim 1, wherein:

the first diaphragm further comprises a diaphragm stiffening structure; and said diaphragm stiffening structure comprises diaphragm ribs configured to create a supporting scaffold.

13. The crossable interseptal occluder device of claim 12, wherein:

said diaphragm stiffening structure comprises at least one diametrical rib extending along a diameter of said first diaphragm; or said diaphragm stiffening structure comprises at least one circumferentially extending rib; or said diaphragm stiffening structure comprises at least one radially extending rib; or said diaphragm stiffening structure comprises at least one rib extending along a circle chord.

14. The crossable interseptal occluder device of claim 1, wherein:

the first diaphragm comprises a diaphragm external annular continuous portion directly or indirectly connected to said support structure, and each opposite elongated body end is connected to said diaphragm external annular continuous portion; or the first diaphragm comprises a diaphragm external annular continuous portion directly or indirectly connected to said support structure, and each opposite elongated body end is in one piece with said diaphragm external annular continuous portion; or the first diaphragm comprises a diaphragm external annular continuous portion directly or indirectly connected to said support structure, the first diaphragm comprises a diaphragm central disc portion, and said plurality of occluding bridges are radially disposed with an external end connected to said diaphragm external annular continuous portion and an internal end connected to said diaphragm central disc portion; or the first diaphragm comprises a diaphragm external annular continuous portion directly or indirectly connected to said support structure, the first diaphragm comprises a diaphragm central disc portion, said plurality of occluding bridges are radially disposed with an external end connected to said diaphragm external annular continuous portion and an internal end connected to said diaphragm central disc portion, and the opposite longitudinal edges are converging towards said diaphragm central disc portion.

15. The crossable interseptal occluder device of claim 1 wherein said support structure is in one piece.

16. The crossable interseptal occluder device of claim 1, wherein said first diaphragm is obtained by a single foil and wherein said opposite longitudinal edges are made by laser cuts.

17. The crossable interseptal occluder device of claim 1, wherein said first diaphragm is made of silicone, a medical elastomer, a polyurethane, or a bio-erodible material.

18. The crossable interseptal occluder device of claim 1, wherein said first diaphragm is made of elastic material capable of a deformation of at least 150%.

19. The crossable interseptal occluder device of claim 1, wherein the plurality of occluding bridges is at least five occluding bridges.

* * * * *